US012751689B2

(12) United States Patent
Tsou et al.

(10) Patent No.: US 12,751,689 B2
(45) Date of Patent: Oct. 6, 2026

(54) ULTRASONIC NEEDLE LOCALIZATION

(71) Applicant: FUJIFILM SONOSITE, INC., Bothell, WA (US)

(72) Inventors: Jean Tsou, Seattle, WA (US); Wei (Grace) Li, Bothell, WA (US); Jimin Zhang, Bellevue, WA (US); Adrian Prokop, Seattle, WA (US); Ryan Hammond, Tacoma, WA (US); Yong Zhou, Woodinville, WA (US); Thomas Endres, Sagle, ID (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 0 days.

(21) Appl. No.: 18/737,516

(22) Filed: Jun. 7, 2024

(65) Prior Publication Data

US 2025/0375182 A1 Dec. 11, 2025

(51) Int. Cl.
*A61B 8/08* (2006.01)
*A61B 8/00* (2006.01)
*A61B 34/20* (2016.01)

(52) U.S. Cl.
CPC .......... *A61B 8/0841* (2013.01); *A61B 8/4254* (2013.01); *A61B 8/4472* (2013.01); *A61B 8/463* (2013.01); *A61B 8/5207* (2013.01); *A61B 8/56* (2013.01); *A61B 8/58* (2013.01); *A61B 34/20* (2016.02); *A61B 2034/2063* (2016.02)

(58) Field of Classification Search
CPC ... A61B 8/0841; A61B 8/4254; A61B 8/4472; A61B 8/463; A61B 8/5207; A61B 8/56; A61B 8/58; A61B 34/20; A61B 2034/2063
See application file for complete search history.

(56) References Cited

U.S. PATENT DOCUMENTS

| | | | | |
|---|---|---|---|---|
| 10,588,595 | B2 * | 3/2020 | Vignon | A61B 8/5269 |
| 2008/0194960 | A1 * | 8/2008 | Randall | A61B 8/4411<br>600/459 |
| 2010/0249600 | A1 * | 9/2010 | Kudoh | A61B 8/565<br>600/459 |
| 2010/0298705 | A1 * | 11/2010 | Pelissier | A61B 8/4254<br>600/443 |
| 2011/0245659 | A1 * | 10/2011 | Ma | A61B 8/0841<br>600/424 |

(Continued)

*Primary Examiner* — Adil Partap S Virk
(74) *Attorney, Agent, or Firm* — Womble Bond Dickinson (US) LLP

(57) ABSTRACT

Ultrasound systems and methods that include and/or use interventional instruments (e.g., needles) are disclosed. In some embodiments, the ultrasound system has an interventional instrument having the at least one ultrasound transducer element attached to the interventional instrument and configured for insertion towards the patient anatomy as part of an insertion procedure. The ultrasound system is configured to: determine, during the insertion procedure, an occurrence of a trigger event; instruct, responsive to the determination of the occurrence of the trigger event, the at least one ultrasound transducer element to transmit the additional ultrasound; and determine, based on the reception of the additional ultrasound by the ultrasound scanner, that the interventional instrument is detected.

21 Claims, 17 Drawing Sheets

(56) References Cited

U.S. PATENT DOCUMENTS

| | | | | |
|---|---|---|---|---|
| 2014/0058266 | A1* | 2/2014 | Call | G01S 15/8915 600/443 |
| 2014/0257080 | A1* | 9/2014 | Dunbar | A61B 5/062 600/409 |
| 2014/0257104 | A1* | 9/2014 | Dunbar | A61B 8/4254 600/443 |
| 2015/0011871 | A1* | 1/2015 | Bradley | A61N 1/36153 600/424 |
| 2015/0119701 | A1* | 4/2015 | Vignon | A61B 8/14 600/424 |
| 2015/0173706 | A1* | 6/2015 | Andrews | A61B 8/463 600/424 |
| 2015/0289839 | A1* | 10/2015 | Saito | A61B 8/465 600/424 |
| 2015/0320439 | A1* | 11/2015 | Andrews | A61B 8/523 600/461 |
| 2016/0008074 | A1* | 1/2016 | Glossop | A61B 90/11 606/130 |
| 2016/0038119 | A1* | 2/2016 | Desjardins | A61B 8/4444 600/424 |
| 2016/0135780 | A1* | 5/2016 | Vignon | G06T 7/0012 600/424 |
| 2016/0354112 | A1* | 12/2016 | Kustra | A61B 34/20 |
| 2016/0367322 | A1* | 12/2016 | Jain | G01S 15/74 |
| 2018/0116629 | A1* | 5/2018 | Boctor | A61B 8/0841 |
| 2019/0029644 | A1* | 1/2019 | Nishigaki | A61B 8/4494 |
| 2020/0008775 | A1* | 1/2020 | Erkamp | A61B 8/4263 |
| 2020/0069290 | A1* | 3/2020 | Kim | A61B 17/3403 |
| 2020/0155118 | A1* | 5/2020 | Anderson | G06T 7/254 |
| 2020/0187981 | A1* | 6/2020 | Tian | A61B 8/0841 |
| 2020/0205775 | A1* | 7/2020 | Duffy | A61B 8/4245 |
| 2021/0161612 | A1* | 6/2021 | Black | A61B 17/3403 |
| 2021/0212658 | A1* | 7/2021 | McGrath | A61B 8/145 |
| 2021/0251599 | A1* | 8/2021 | Torp | A61B 8/488 |
| 2021/0259658 | A1* | 8/2021 | Jain | A61B 8/0841 |
| 2022/0032089 | A1* | 2/2022 | Curra | G01S 7/2922 |
| 2022/0039829 | A1* | 2/2022 | Zijlstra | A61B 8/462 |
| 2022/0061932 | A1* | 3/2022 | Visser | A61B 8/5292 |
| 2022/0133280 | A1* | 5/2022 | Urabe | A61B 8/463 600/443 |
| 2022/0142608 | A1* | 5/2022 | Matsumoto | A61B 8/0841 |
| 2023/0131115 | A1* | 4/2023 | Halmann | A61B 8/481 600/424 |
| 2023/0190238 | A1* | 6/2023 | Matsumoto | A61B 8/54 600/443 |

* cited by examiner

1700

ULTRASONIC NEEDLE LOCALIZATION

FIELD

Embodiments disclosed herein relate to ultrasound systems. More specifically, embodiments disclosed herein are related to ultrasound devices that include and/or use interventional instruments (e.g., needles).

BACKGROUND

Ultrasound systems can generate ultrasound images by transmitting sound waves at frequencies above the audible spectrum into a body, receiving echo signals caused by the sound waves reflecting from internal body parts, and converting the echo signals into electrical signals for image generation. Because they are non-invasive and non-ionizing, ultrasound systems are used ubiquitously. One example where ultrasound systems are used is to provide visual guidance when inserting an interventional instrument, such as a needle, into a patient anatomy.

Ultrasound-guided needle placement, and more specifically needle tip placement, is one of the most often used applications in ultrasound, including for biopsies, anesthesiology (e.g., nerve block), peripheral intravenous insertion, and the like. However, visualization of the needle tip position with conventional ultrasound systems is often poor when the needle tip location is deep, the needle tip is out of the imaging plane, or the needle angle with respect to the transducer array is large (especially for curved arrays). Hence, for ultrasound needle guidance procedures, it is difficult to track the needle progress during insertion, and, thus, know where the needle tip is relative to the image plane (and the desired target). Therefore, patients may be subject to multiple, painful insertions and may not receive the best care possible.

SUMMARY

Ultrasound systems and methods that include and/or use interventional instruments (e.g., needles) are disclosed. In some embodiments, the ultrasound system has an ultrasound scanner configured to transmit ultrasound at a patient anatomy, receive reflections of the ultrasound from the patient anatomy, and receive additional ultrasound from at least one ultrasound transducer element and an interventional instrument having the at least one ultrasound transducer element attached to the interventional instrument and configured for insertion towards the patient anatomy as part of an insertion procedure. The ultrasound system also has a processor system configured to: determine, during the insertion procedure, an occurrence of a trigger event; instruct, responsive to the determination of the occurrence of the trigger event, the at least one ultrasound transducer element to transmit the additional ultrasound; and determine, based on the reception of the additional ultrasound by the ultrasound scanner, that the interventional instrument is detected. The ultrasound system further includes a display device configured to display an ultrasound image of the patient anatomy based on the reflections of the ultrasound and a visual representation that indicates the detection of the interventional instrument.

In some other embodiments, the ultrasound system has a multi-array ultrasound scanner having a first array configured to transmit ultrasound at a patient anatomy and receive reflections of the ultrasound from the patient anatomy, and a second array configured to transmit additional ultrasound at an interventional instrument and receive additional reflections of the additional ultrasound from the interventional instrument, where the interventional instrument is configured for insertion towards the patient anatomy as part of an insertion procedure. The ultrasound system also includes a processor system and a display device. The processor system is configured to determine at a time of the insertion procedure that the interventional instrument is detected by the second array based on the additional reflections and is not yet detected by the first array based on the reflections. The display device is configured to display an ultrasound image of the patient anatomy based on the reflections and a visual representation that indicates the detection of the interventional instrument by the second array.

In yet some other embodiments, the ultrasound system has an ultrasound scanner having an array configured to transmit ultrasound and receive reflections of the ultrasound, an interventional instrument configured for patient insertion as part of an insertion procedure, a processor system, and a display device. The processor system is configured to: cause the ultrasound scanner to transmit the ultrasound as interleaved variable-width elevational planes; generate an ultrasound image based on the reflections of the ultrasound from a first phase of the interleaving; and detect the interventional instrument based on the reflections of the ultrasound from one or more other phases of the interleaving. The display device is configured to display the ultrasound image and a visual representation that indicates the detection of the interventional instrument.

Other aspects and advantages of the embodiments will become apparent from the following detailed description taken in conjunction with the accompanying drawings which illustrate, by way of example, the principles of the described embodiments.

BRIEF DESCRIPTION OF THE DRAWINGS

The appended drawings illustrate examples and are, therefore, exemplary embodiments and not considered to be limiting in scope.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

For ultrasound needle guidance procedures, it is difficult to track the needle progress during insertion, and, thus, know where the needle tip is relative to the image plane (and the desired target) with conventional ultrasound systems. Therefore, patients may be subject to multiple, painful insertions and may not receive the best care possible. Accordingly, some embodiments disclosed herein include systems, devices, and methods for needle and/or needle tip localization, including detection, visualization, tracking, and guidance. In some embodiments, an ultrasound system includes a needle having one or more transducer elements attached to it that can transmit and/or receive ultrasound for ultrasonic needle localization. Additionally or alternatively, in aspects, an ultrasound system includes a multi-array ultrasound scanner having a first array configured to transmit ultrasound at a patient anatomy and receive reflections of the ultrasound from the patient anatomy. In some embodiments, the multi-array ultrasound scanner also includes a second array configured to transmit additional ultrasound at an interventional instrument (e.g., a needle) and receive additional reflections of the additional ultrasound from the interventional instrument for ultrasonic needle localization. Additionally or alternatively, in some embodiments, an ultrasound system includes a processor to cause an ultrasound scanner to transmit the ultrasound as variable-width elevational planes for ultrasonic needle localization. In some embodiments, the variable-width elevational planes are interleaved and transmitted from an ultrasound scanner having a single array. Additionally or alternatively, the variable-width elevational planes can be transmitted from different arrays of a multi-array ultrasound scanner.

Figure 1:
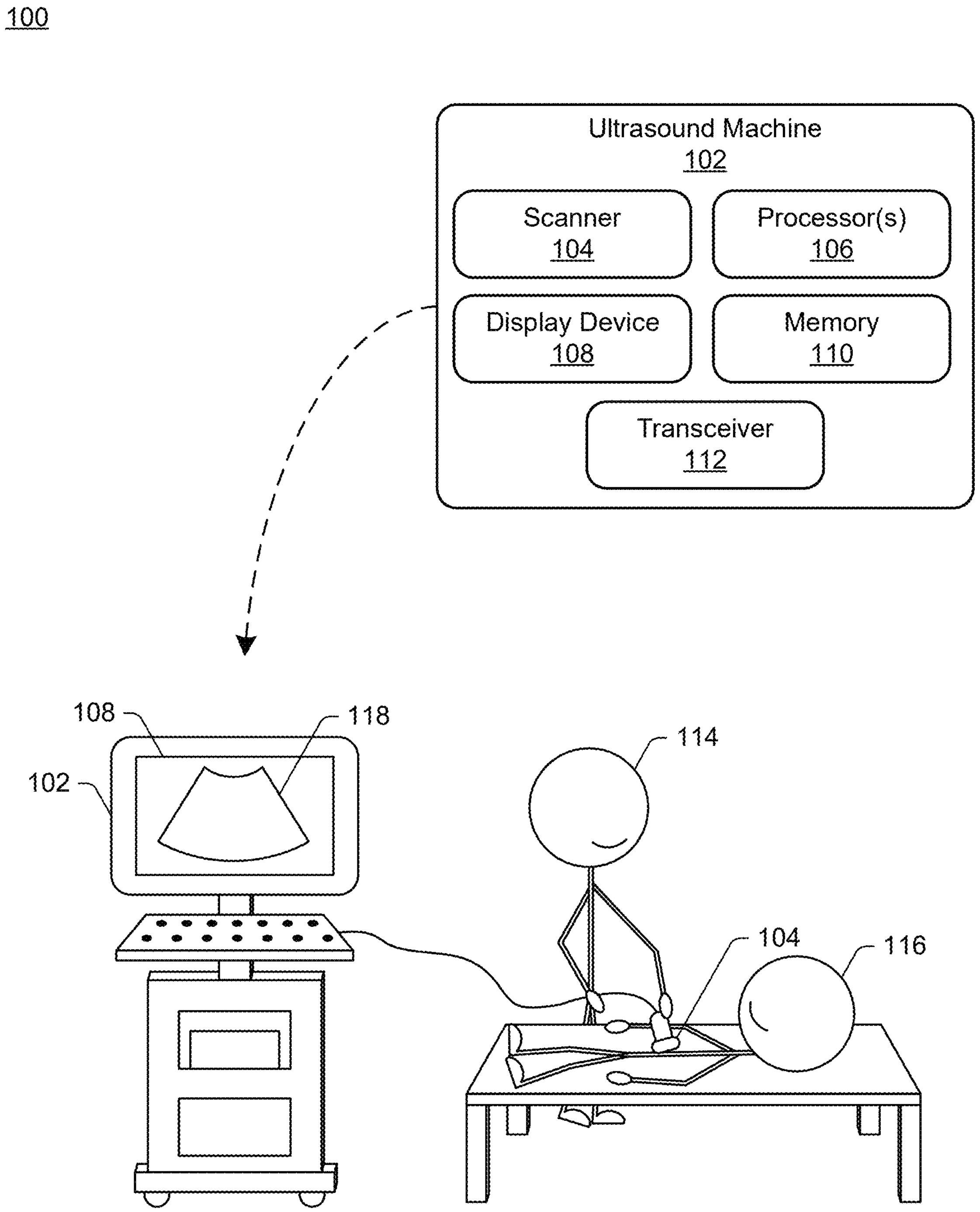
FIG. 1 illustrates some embodiments of an ultrasound system in an environment for ultrasonic needle localization during an ultrasound examination.

FIG. 1 illustrates an ultrasound system in an environment 100 for ultrasonic needle localization during an ultrasound examination. A needle is used throughout this specification as an example of an interventional instrument that can be localized. Other examples of interventional instruments that can be localized by an ultrasound system configured according to some embodiments include a catheter, stint, clamp, guide, etc. Needle localization in accordance with embodiments described herein can include one or more of needle and/or needle tip detection, visualization, tracking, and guidance.

The ultrasound system in FIG. 1 includes an ultrasound machine 102 and an ultrasound scanner 104. The ultrasound machine 102 generates high-frequency sound waves (e.g., ultrasound) and imaging data based on the ultrasound reflecting off a patient anatomy/body structure and/or an interventional instrument. The ultrasound machine 102 includes various components, some of which include the scanner 104, one or more processors 106, a display device 108, a memory 110, and a transceiver 112.

A user 114 (e.g., nurse, ultrasound technician, operator, sonographer, clinician, etc.) directs the scanner 104 toward a patient 116 to non-invasively scan internal bodily structures (e.g., patient anatomies such as organs, tissues, bones, etc.) of the patient 116 for testing, diagnostic, therapeutic, or procedural reasons, including a needle insertion procedure. In some embodiments, the scanner 104 includes an ultrasound transducer array and electronics communicatively coupled to the ultrasound transducer array to transmit ultrasound signals to the patient's anatomy and receive ultrasound signals reflected from the patient's anatomy. In some embodiments, the scanner 104 is an ultrasound scanner, which can also be referred to as an ultrasound probe or transducer. In some embodiments, the scanner 104 is a multi-array scanner.

The display device 108 is coupled to the processor 106, which can include any suitable processor, number of processors, or processor system, such as one or more central processing units (CPUs), graphics processing units (GPUs), vector processors, Reduced Instruction Set Computer (RISC) processors, Reduced Instruction Set Computer (CISC) processors, very long instruction word (VLIW) processors, etc. The processor 106 can execute instructions stored on memory 110 to perform operations disclosed herein for ultrasonic needle localization. For example, the processor 106 can process the reflected ultrasound signals to generate ultrasound data, including an ultrasound image. The display device 108 is configured to generate and display an ultrasound image (e.g., ultrasound image 118) of the anatomy and/or interventional instrument based on the ultrasound data generated by the processor 106 from the reflected ultrasound signals detected by the scanner 104. In some embodiments, the ultrasound data includes the ultrasound image 118 or data representing the ultrasound image 118. The transceiver 112 can be configured to transmit, e.g., over a network maintained by a care facility, the ultrasound data and/or any data related to the ultrasound examination, such as medical worksheet data, to a medical archiver (e.g., a vendor neutral archive (VNA)). In some embodiments, the transceiver 112 can receive data from the medical archiver, such as, for example, but not limited to, patient history data or previous examination data.

Figure 2:
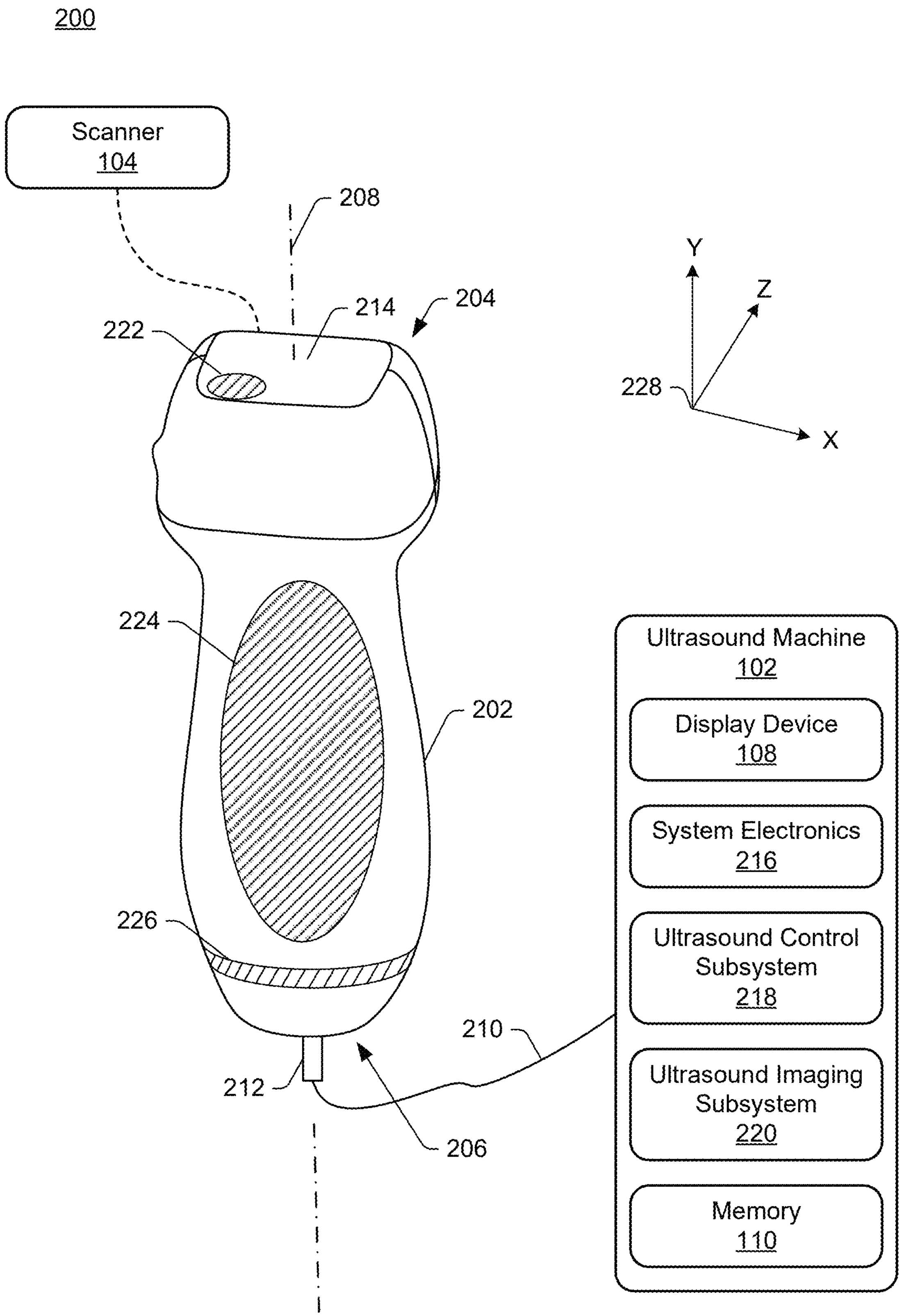
FIG. 2 illustrates some embodiments of an implementation of the ultrasound system from FIG. 1.

FIG. 2 illustrates an example implementation 200 of some embodiments of the ultrasound system illustrated in the environment 100 of FIG. 1. Referring to FIG. 2, in the implementation 200, the scanner 104 (e.g., ultrasound scanner) includes an enclosure 202 extending between a distal end portion 204 and a proximal end portion 206. The enclosure 202 includes a central axis 208 (e.g., longitudinal axis) that intersects the distal end portion 204 and the proximal end portion 206. The central axis 208 corresponds to an axial direction of the scanner 104. The scanner 104 is electrically coupled to an ultrasound imaging system (e.g., the ultrasound machine 102) via a coupling 210. In some embodiments, the coupling 210 includes a cable that is attached to the proximal end portion 206 of the scanner 104 by a strain-relief element 212. In some embodiments, the coupling 210 includes a wireless coupling so that the scanner 104 is wirelessly coupled to the ultrasound imaging system and communicates with the ultrasound imaging system via one or more wireless transmitters, receivers, or transceivers over a wireless connection or network (e.g., Bluetooth™, Wi-Fi™, etc.).

A transducer assembly 214 having one or more transducer elements is electrically coupled to system electronics 216 in the ultrasound machine 102. In operation, the transducer assembly 214 transmits ultrasound energy from the one or more transducer elements toward a subject and receives ultrasound echoes from the subject. The ultrasound echoes are converted into electrical signals by the transducer element(s) and electrically transmitted to the system electronics 216 in the ultrasound machine 102 for processing and generation of one or more ultrasound images.

Capturing ultrasound data from a subject using a transducer assembly (e.g., the transducer assembly 214) generally includes generating ultrasound signals, transmitting ultrasound signals into the subject, and receiving ultrasound signals reflected by the subject. A wide range of frequencies of ultrasound can be used to capture ultrasound data, such as, for example, low-frequency ultrasound (e.g., less than 15 Megahertz (MHz)) and/or high-frequency ultrasound (e.g., greater than or equal to 15 MHz). A particular frequency range to use can readily be determined based on various factors, including, for example, depth of imaging, desired resolution, and so forth.

In some embodiments, the system electronics 216 include one or more processors (e.g., the processor(s) 106 from FIG. 1), integrated circuits, application-specific integrated circuits (ASICs), Field Programmable Gate Arrays (FPGAs), and power sources to support functioning of the ultrasound machine 102. In some embodiments, the ultrasound machine 102 also includes an ultrasound control subsystem 218 having one or more processors. At least one processor, FPGA, or ASIC can cause electrical signals to be transmitted to the transducer(s) of the scanner 104 to emit sound waves and also receives electrical pulses from the scanner 104 that were created from the returning echoes. One or more processors, FPGAs, or ASICs can process the raw data associated with the received electrical pulses and form an image that is sent to an ultrasound imaging subsystem 220, which causes the image (e.g., the image 118 in FIG. 1) to be displayed via the display device 108. Thus, the display device 108 displays ultrasound images from the ultrasound data processed by the processor(s) of the ultrasound control subsystem 218.

In some embodiments, the ultrasound machine 102 also includes one or more user input devices (e.g., a keyboard, a cursor control device, a microphone, a camera, touchscreen, etc.) that input data and enable taking measurements from the display device 108 of the ultrasound machine 102. The ultrasound machine 102 can also include a disk storage device (e.g., computer-readable storage media such as read-only memory (ROM), a Flash memory, a dynamic random-access memory (DRAM), a NOR memory, a static random-access memory (SRAM), a NAND memory, and so on) for storing the acquired ultrasound data. In aspects, the disk storage device includes the memory 110, which is local to the ultrasound machine 102. Alternatively, the memory 110 used for storing the acquisition data can be remote, such as on a remote server communicatively connected to the ultrasound machine 102. In addition, the ultrasound machine 102 can include a printer that prints the image from the displayed data. To avoid obscuring the techniques described herein, such user input devices, disk storage device, and printer are not shown in FIG. 2.

The ultrasound scanner 104 in the implementation 200 also includes one or more pressure sensors 222 on the lens of the scanner 104, and one or more pressure sensors 224 on the enclosure 202 of the scanner 104. The pressure sensors 222 and 224 can include in, on, or under a sensor region any suitable type of sensors for determining a pressure. In one example, the pressure sensors 222 and 224 includes capacitive sensors that can measure a capacitance, or change in capacitance, caused by a user's touch or proximity of touch, as is common in touchscreen technologies. The pressure sensors 222 and 224 can generate sensor data indicative of a touch or pressure. The sensor data can include a binary indicator that indicates the presence and absence of a touch on the sensor. For instance, a "1" for sensor data can indicate that a pressure is sensed at the pressure sensor, and a "0" for the sensor data can indicate that a pressure is not sensed at the pressure sensor. Additionally or alternatively, the sensor data can include a multi-level indicator that indicates an amount of pressure on the sensor, such as an integer scale from zero to five. For instance, a "0" can indicate that no pressure is detected at the sensor, and a "1" can indicate a small amount of pressure is detected at the sensor. A "2" can indicate a larger amount of pressure is detected at the sensor than a "1", and a "5" can indicate a maximum amount of pressure is detected at the sensor.

The pressure sensors 222 and 224 are illustrated in FIG. 2 as ellipses for clarity, and generally can be of any suitable shape and size, and generate sensor data indicating pressure at any suitable number of points. For instance, in one example, the pressure sensors 222 cover an exterior surface of the lens of the scanner 104 and can be used to determine when the scanner is placed against a patient. Additionally or alternatively, the pressure sensors 224 can substantially cover the enclosure 202 of the scanner 104 and can be used to determine when a clinician grabs the scanner 104 for use in an ultrasound examination (e.g., the clinician has a suitable grip on the scanner 104 to perform the ultrasound examination). The ultrasound system can use the sensor data from one or both of the pressure sensors 222 and 224 to generate a trigger signal that can be used for ultrasonic needle localization. For instance, in some embodiments, a needle can include one or more ultrasound transducers, e.g., at the tip of the needle (discussed below in more detail with respect to FIG. 3). When the sensor data from one or both of the pressure sensors 222 and 224 is above a threshold level, and/or the sensor data from the pressure sensors 224 indicate a grip pattern indicative of a human operating the scanner, the system can generate a trigger signal. The trigger signal can be used to activate the one or more ultrasound transducers at the tip of the needle so that they transmit ultrasound that can be detected by the scanner 104, and thus used to detect and/or visualize the tip of the needle.

In some embodiments, the scanner 104 includes an inertial measurement unit (IMU) 226 for generating positional data that determines a position and orientation of the scanner 104 in a coordinate system, e.g., the coordinate system 228 in FIG. 2. The IMU 226 can include a combination of accelerometers, gyroscopes, and magnetometers, and generate positional data including data representing six degrees of freedom (6DOF), such as yaw, pitch, and roll angles in a coordinate system. Typically, 6DOF refers to the freedom of movement of a body in three-dimensional space. For example, the body is free to change position as forward/backward (surge), up/down (heave), left/right (sway) translation in three perpendicular axes, combined with changes in orientation through rotation about three perpendicular axes, often termed yaw (normal axis), pitch (transverse axis), and roll (longitudinal axis). Additionally or alternatively, the ultrasound system can include a camera and fiducial markers on the ultrasound scanner 104 (not shown in FIG. 2) to determine the positional data for the ultrasound scanner 104. In some embodiments, the system generates, based on the positional data, the trigger signal to activate the one or more ultrasound transducers at the tip of the needle so that they transmit ultrasound that can be detected by the scanner 104, and thus used to detect and/or visualize the tip of the needle. For instance, the positional data can indicate that the scanner 104 is within a threshold distance of the patient and/or the needle.

Figure 3:
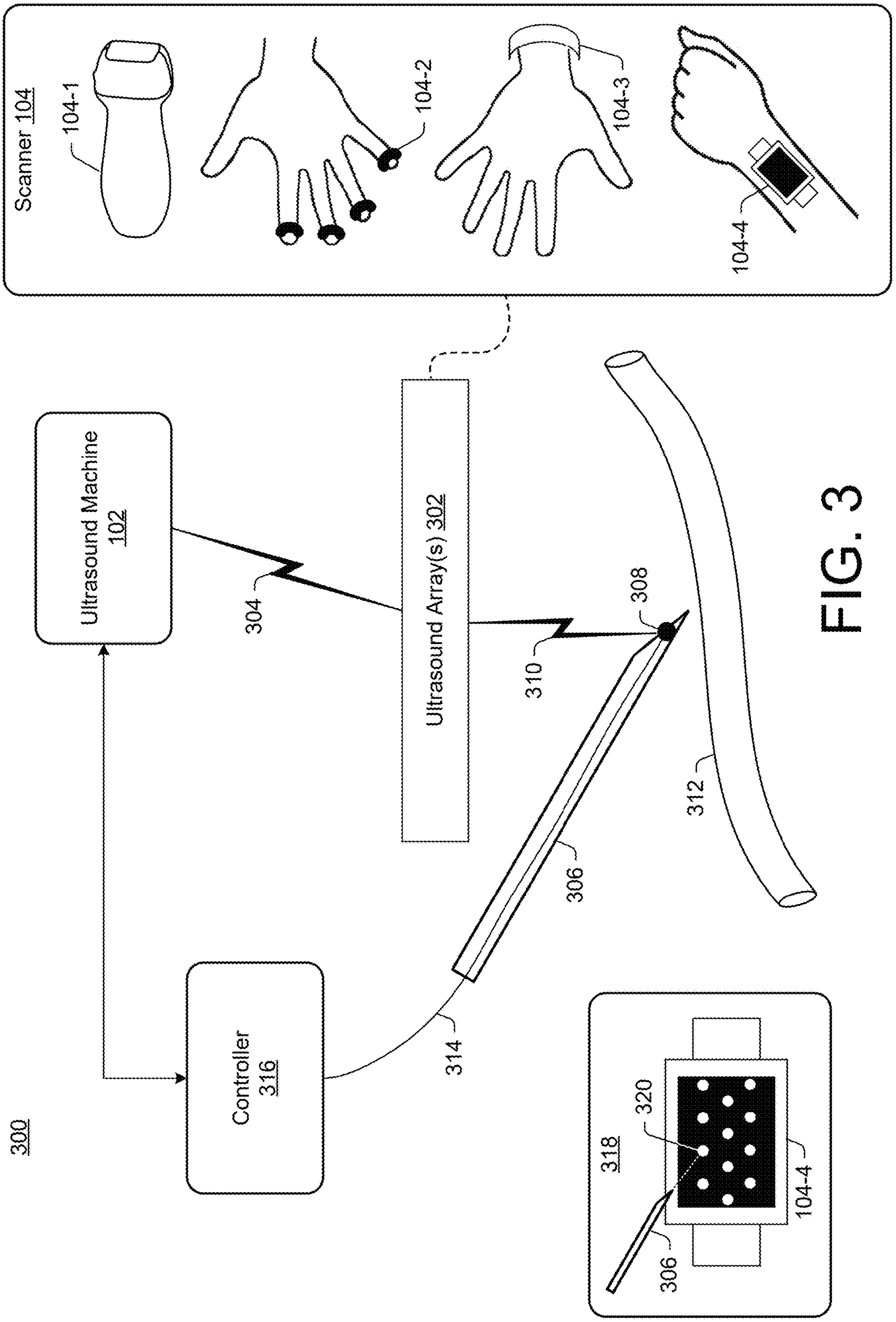
FIG. 3 illustrates some embodiments of an ultrasound system for ultrasonic needle localization.

FIG. 3 illustrates an example ultrasound system 300 for ultrasonic needle localization in accordance with some embodiments. In some embodiments, the ultrasound system 300 includes the ultrasound machine 102 that is coupled to one or more ultrasound arrays 302 via a coupling 304. In aspects, the coupling 304 includes a wireless communication link, so that the scanner 104 can be wirelessly coupled to the ultrasound machine 102. Additionally or alternatively, the coupling 304 can include one or more cables to connect the scanner 104 to the ultrasound machine 102.

The one or more ultrasound arrays 302 can include any suitable number and type of transducer arrays, such as linear, curvilinear, phased arrays, circular, combinations thereof, and the like, and can be included in any type of ultrasound scanner 104. The ultrasound system 300 includes various examples of the ultrasound scanner 104 that can include the one or more ultrasound arrays 302, including a handheld probe 104-1, e.g., the one or more ultrasound arrays 302 can be contained in the distal end portion 204 of the handheld probe 104-1. In some embodiments, the ultrasound scanner 104 includes wearable form factors, including rings 104-2, a wristband 104-3, and a patch 104-4. In some embodiments, the wearable form factors can be worn by a patient (e.g., the patch 104-4). Additionally or alternatively, the wearable form factors can be worn by an operator of the ultrasound system, such as the rings 104-2.

In some embodiments, wearable form factors of the scanner 104 include windows (e.g., holes) through which a needle can be inserted. For example, inset 318 illustrates the patch 104-4 having a set of holes 320, and the needle 306 is being inserted through one of the holes. Hence, the physician's hands are free to perform the needle procedure, unencumbered by holding the scanner 104. In some embodiments, the ultrasound system recommends one of the holes 320 for needle insertion to the user (e.g., physician). For example, the system can image the patient anatomy with the patch 104-4. The user can designate a region of interest (ROI) that includes the patient anatomy. Additionally or alternatively, the system can include a machine-learned model (e.g., a neural network) trained to identify the patient anatomy and determine the ROI that includes the patient anatomy. Further, the system can include a machine-learned model to generate the recommendation of one of the holes 320 for needle insertion. Based on the ROI and its position relative to the patch 104-4, the system can recommend one of the holes 320 for a needle insertion so that the needle 306 intersects the ROI at a proper angle and location. For example, in some embodiments, the system includes a user interface that displays the pattern of holes 320, with the recommended hole highlighted, e.g., blinking. Note that in some embodiments, the angle is user selectable with a 45° angle between the hole location and the target anatomy being the default. Other angles could be set as the default.

In some embodiments, the ultrasound system 300 also includes the needle 306 that includes one or more ultrasound transducers 308, e.g., at the tip of the needle. In some embodiments, the one or more ultrasound transducers 308 include a single transducer element and no other transducer elements. The one or more ultrasound transducers 308 can include any suitable type of transducer elements, including lead zirconate titanate (PZT), which is a piezoelectric ceramic material, a piezoelectric micro-machined ultrasonic transducer (PMUT), or a capacitive micro-machined ultrasonic transducer (CMUT). In aspects of ultrasonic needle localization, in some embodiments, the one or more ultrasound transducers 308 are implemented to generate ultrasound 310 that can be received by the ultrasound arrays 302 to localize, visualize, and/or detect the tip of the needle 306, such as for insertion into a blood vessel 312. Additionally or alternatively, the ultrasound arrays 302 can generate the ultrasound 310 that is received by the one or more ultrasound transducers 308 so that the system can localize, visualize, and/or detect the tip of the needle 306.

The one or more ultrasound transducers 308 can be affixed to any suitable portion of the needle 306. As is illustrated in FIG. 3, in aspects of ultrasonic needle localization, in some embodiments, a transducer element of the one or more ultrasound transducers 308 can be affixed to a tip of the needle 306, inside the bevel of the needle and oriented to point upwards, e.g., towards the ultrasound arrays 302 when the needle 306 is inserted into the patient. In contrast, if the transducer element, e.g., a single transducer element, was affixed at the bottom underneath the bevel, the needle itself could act to interfere with the ultrasound transmitted by the transducer element and hinder reception by the ultrasound arrays 302. Further, the transducer element would be subjected to pressure from tissue during insertion and could be damaged or accidentally removed from the needle 306. In some embodiments, the needle 306 includes a marker that can be used as a registration mark to determine the rotational angle of the needle 306 (e.g., about the longitudinal axis of the needle) when it is inserted, so that the one or more ultrasound transducers 308 can be pointed towards the ultrasound arrays 302.

In some embodiments, the one or more ultrasound transducers 308 includes a single element transducer. In some embodiments, the single element transducer includes a single element transducer of approximately 0.2 mm that can radiate sufficient power to be received by the transducer array 302. The size of the single element transducer is sufficiently small to fit inside the needle 306. In some embodiments, the frequency of the single element transducer can be dependent on the depth desired for the application (e.g., a lower frequency can be used for deeper penetrations, a higher frequency can be used for shallower penetrations, etc.). In some embodiments, the gauge and length of the needle can determine the single element transducer to use. For example, for a 10 cm biopsy for the deep abdomen, a 3-4 MHz transducer can be used. In other words, the intended use or examination can determine the transducer that may be appropriate.

In some embodiments, the one or more ultrasound transducers 308 include an annular array affixed around the circumference of the needle 306, so that the needle 306 can be inserted invariant to rotation (e.g., with respect to the longitudinal axis of the needle) while still having a transducer element of the one or more ultrasound transducers 308 pointing to the ultrasound arrays 302. In aspects, the one or more ultrasound transducers 308 comprise a ceramic coating placed at least partially around the needle 306.

The one or more ultrasound transducers 308 can be affixed to the needle 306 by any suitable means. In some embodiments, the one or more ultrasound transducers 308 are attached to the needle 306 with a bonding agent, such as a glue or another adhesive. Additionally or alternatively, the one or more ultrasound transducers 308 can be affixed to the needle 306 via a cut-out or hole machined into the needle 306. The one or more ultrasound transducers 308 can be "snapped" into the cut-out/hole. In some embodiments, the one or more ultrasound transducers 308 include a top portion and a bottom portion that mates to the top portion through the cut-out/hole of the needle 306 to secure the one or more ultrasound transducers 308 to the needle 306. The two portions can snap together, screw together, be glued together, combinations thereof, and the like. In some embodiments, the ultrasound transducers 308, such as, for example, MEMS-based piezoelectric ultrasonic transducers (e.g., piezoelectric micromachined ultrasonic transducers (PMUT), capacitive MUT (CMUT), etc.), or film-based transducers are deposited on the needle 306. In some embodiments, the ultrasound system includes a sheath to encapsulate the one or more ultrasound transducers 308 and prevent them from falling off the needle 306 during an insertion procedure. The sheath can be inserted over the combination of the one or more ultrasound transducers 308 and the needle 306. In some embodiments, the needle 306 is covered with a coating (e.g., Parylene, etc.).

In some embodiments, the ultrasound system 300 also includes a connector 314 to electronically connect the one or more ultrasound transducers 308 to a controller 316. The connector 314 can include a wire that traverses the length of the needle 306 to reach the one or more ultrasound transducers 308. For instance, the wire can be run inside the shaft of the needle 306. In another example, the wire can be affixed to the outside surface of the needle 306. In some embodiments, the controller 316 provides power and/or data to the one or more ultrasound transducers 308 via the connector 314. For example, the controller 316 can provide transmit pulses to the one or more ultrasound transducers 308 to configure the one or more ultrasound transducers 308 to transmit ultrasound 310 that can be received by the ultrasound arrays 302. In some embodiments, the controller 316 also receives data from the one or more ultrasound transducers 308 via the connector 314, such as ultrasound data received by the one or more ultrasound transducers 308 that was transmitted by the ultrasound arrays 302. In some embodiments, the connector 314 includes a wireless communication link, so that the controller 316 can be wirelessly connected to the one or more ultrasound transducers 308.

The controller 316 can include any suitable processor to process data received from the one or more ultrasound transducers 308, or to generate data to send to the one or more ultrasound transducers 308. For instance, the controller can include a microcontroller, CPU, GPU, vector processor, RISC processor, CISC processor, VLIW processor, and the like. In some embodiments, the controller 316 includes a synchronization circuit to synchronize the operation of the one or more ultrasound transducers 308 on the needle 306 with the operation of the ultrasound arrays 302 of the scanner 104. For example, the synchronization circuit can instruct the one or more ultrasound transducers 308 to generate and transmit ultrasound data in between ultrasound image frames generated by the ultrasound arrays 302. In another example, the synchronization circuit can instruct the one or more ultrasound transducers 308 to receive ultrasound data from the ultrasound arrays 302 in between ultrasound image frames generated by the ultrasound arrays 302. For instance, the ultrasound arrays 302 can include a first array for generating ultrasound image frames and a second array or element for communicating with the one or more ultrasound transducers 308 to localize the needle 306.

In some embodiments, the synchronization circuit can also include an interrupter circuit configured to instruct the one or more ultrasound transducers 308 not to generate and transmit ultrasound data during ultrasound image frames generated by the ultrasound arrays 302. Accordingly, in some embodiments, the controller 316 is coupled to the ultrasound machine 102, can receive data from the ultrasound machine 102, and can provide data to the ultrasound machine 102.

In some embodiments, the one or more ultrasound transducers 308 operate asynchronously from the ultrasound machine 102 and/or the ultrasound arrays 302. For instance, the one or more ultrasound transducers 308 can receive and/or transmit ultrasound data independent from the timing of image frame data generated by the ultrasound arrays 302. Hence, in some aspects, the controller 316 may not be connected to the ultrasound machine 102.

Figure 4:
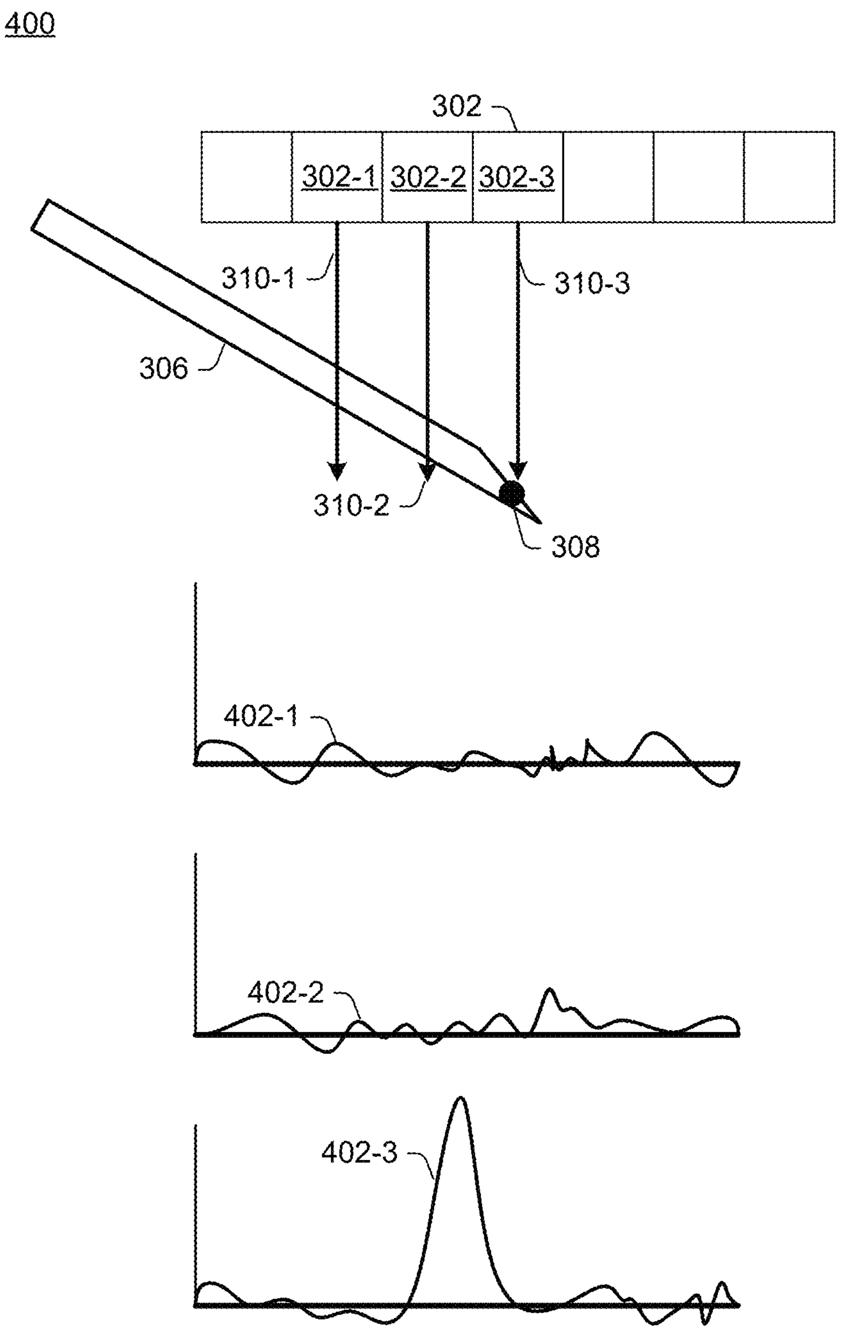
FIG. 4 illustrates waveforms generated by a controller for ultrasonic needle localization in accordance with some embodiments.

In aspects of ultrasonic needle localization, in some embodiments, the one or more ultrasound transducers 308 are implemented to receive ultrasound 310 transmitted by the ultrasound array 302. Additionally or alternatively, the one or more ultrasound transducers 308 can be implemented to transmit ultrasound 310 that can then be received by the ultrasound arrays 302. Hence, the controller 316 can detect and/or image the position of the tip of the needle 306 based on the ultrasound 310 received by the one or more ultrasound transducers 308 and/or the ultrasound arrays 302. For example, FIG. 4 illustrates waveforms 400 generated by the controller 316 for ultrasonic needle localization in accordance with some embodiments.

The waveforms 400 include waveform 402-1, waveform 402-2, and waveform 403-3. In some embodiments, the waveform 402-1 is generated by the controller 316 responsive to the transducer 308 (e.g., a single element transducer) on the tip of the needle 306 receiving the ultrasound 310-1 generated by a first subset of transducer elements 302-1 of the ultrasound array 302. The waveform 402-2 can be generated by the controller 316 responsive to the transducer 308 (e.g., a single element transducer) on the tip of the needle 306 receiving the ultrasound 310-2 generated by a second subset of transducer elements 302-2 of the ultrasound array 302. The waveform 402-3 can be generated by the controller 316 responsive to the transducer 308 (e.g., a single element transducer) on the tip of the needle 306 receiving the ultrasound 310-3 generated by a third subset of transducer elements 302-3 of the ultrasound array 302.

In some other embodiments, the transducer 308 transmits ultrasound, e.g., the ultrasound 310-3, that is received by the ultrasound array 302, and in response, the controller 316 can generate the waveforms 402-1, 402-2, and 403-3. For example, the controller 316 can generate (i) the waveform 402-1 from the ultrasound received by the first subset of transducer elements 302-1, (ii) the waveform 402-2 from the ultrasound received by the second subset of transducer elements 302-2, and (iii) the waveform 402-3 from the ultrasound received by the third subset of transducer elements 302-3.

In still other embodiments, the waveforms 402-1, 402-2, and 403-3 can be generated by the controller 316 and each correspond to a different ultrasound frequency and/or beam width and/or elevational plane transmitted by the ultrasound array(s) 302, as described in more detail below with respect to FIGS. 9 and 10.

Based on the waveforms 400, the system can determine the position of the tip of the needle 306 relative to the ultrasound array 302. For instance, the peak in the waveform 402-3 and lack of peaks in the waveforms 402-1 and 402-2 indicate that the tip of the needle 306 is under the transducer elements 302-3 of the ultrasound array 302, rather than the transducer elements 302-1 and 302-2. In some embodiments, the system can track the motion of the tip of the needle 306 based on the waveforms 400 and can display a trajectory of the needle tip in a user interface of the ultrasound machine 102.

Returning to FIG. 3, as described above, the controller 316 can provide power to the one or more ultrasound transducers 308 via the connector 314. In some embodiments, the power can be supplied by a battery that is coupled to the connector 314. Hence, the power supply used for the one or more ultrasound transducers 308 can be separate from the power supply used for the ultrasound arrays 302 and the ultrasound machine 102. Thus, power that is supplied internal to the patient is not connected to wall power (e.g., 110 Volts, 60 Hz power supplies), and therefore the patient is not exposed to the risk of electrical shock from the wall outlet.

Additionally or alternatively, in some embodiments, the system provides power to the one or more ultrasound transducers 308 remotely (e.g., wirelessly) from outside the patient. For instance, the one or more ultrasound transducers 308 can be powered from an RF source that is outside the patient, such as a hand-held or patient-worn device that inductively couples power to the one or more ultrasound transducers 308. To prevent corruption of the ultrasound received and/or generated by the one or more ultrasound transducers 308, in some embodiments, the ultrasound system includes a compensation system that reduces (e.g., subtracts out) noise based on statistics of the RF power source and/or calibration data obtained via the RF source. In still other embodiments, the one or more ultrasound transducers 308 can be powered by ultrasound transmitted by the ultrasound arrays 302.

The system can generate one or more trigger signals (e.g., wake-up signals) to instruct the one or more ultrasound transducers 308 to transmit the ultrasound 310 and/or receive the ultrasound 310. As described above, examples of trigger signals can be based on pressure of the ultrasound scanner (e.g., via a grip on the scanner or pressure against a patient), as well as based on positional data representing a location and/or orientation of the ultrasound scanner. Another example of a trigger signal includes an acoustic signal in the ultrasound 310 itself received by the one or more ultrasound transducers 308 and transmitted by the ultrasound arrays 302. In some embodiments, the ultrasound 310 includes a known, or predefined sequence, such as a sequence of frequencies, amplitudes, pulse widths, combinations thereof, and the like, to instruct the one or more ultrasound transducers 308 to transmit or receive. The sequence can be constructed so that it causes the needle 306 to resonate, and in response to the resonance, the one or more ultrasound transducers 308 can turn on, to enable transmission and/or reception. In some other embodiments, the trigger signal is based on RF data from an RF source, such as a hand-held, patient-worn device, or device connected to an ultrasound scanner. In still some other embodiments, the controller 316 provides the trigger signal to the one or more ultrasound transducers 308 electronically via the connector 314.

Figure 14:
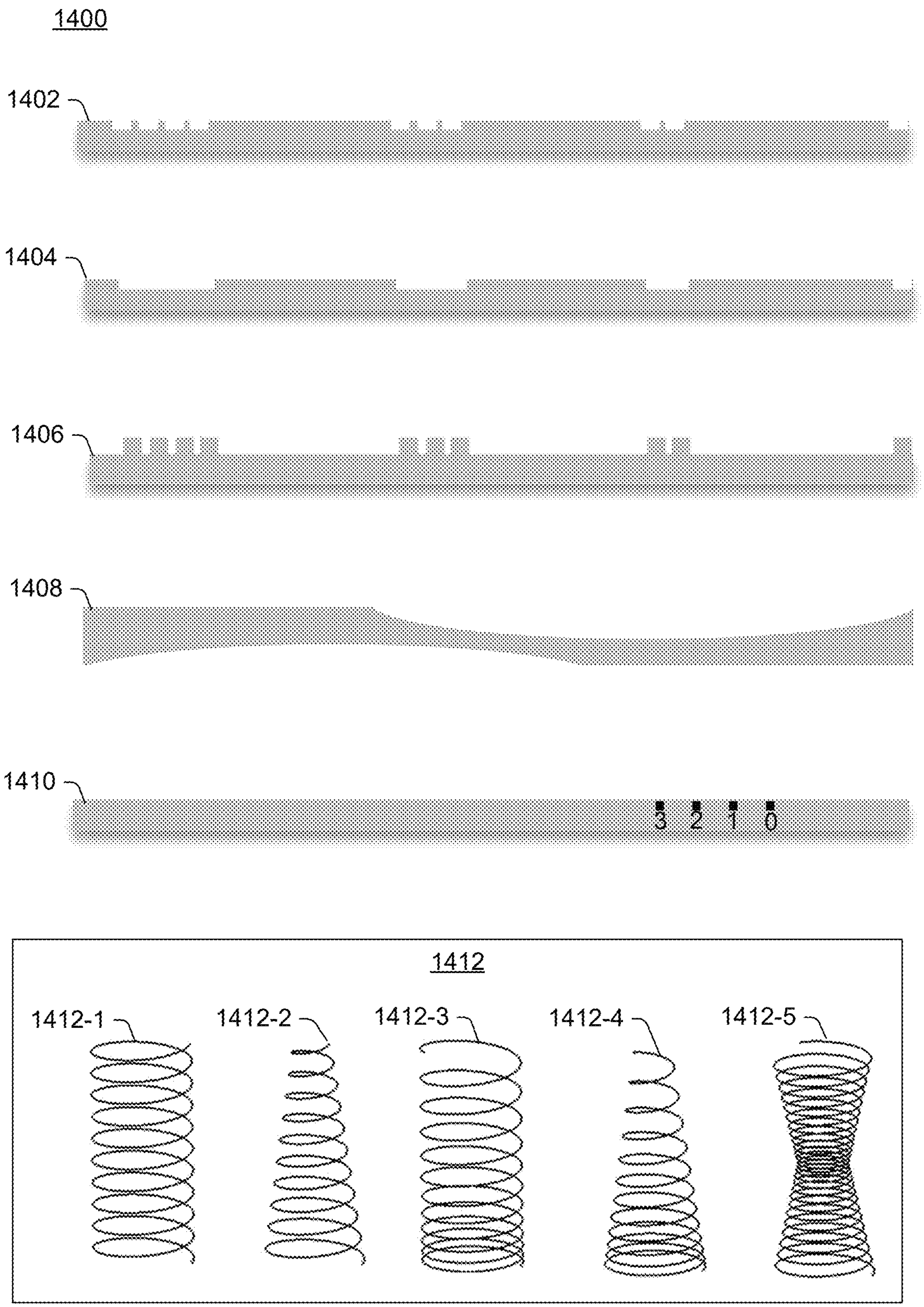
FIG. 14 illustrates example needles for ultrasonic needle localization in accordance with some embodiments.

In some embodiments, the needle 306 includes one or more markings (e.g., markings etched or machined into the needle, or the shape of the needle itself can make up the markings), discussed in more detail below with respect to FIG. 14. The ultrasound array(s) 302 can transmit the ultrasound 310 at the needle 306 and based on the reflections from the needle 306, the controller 316 can decode a meaning of the markings. The markings can indicate that the needle 306 is equipped with the one or more ultrasound transducers 308, and in response to the decoding, the controller 316 can send a trigger signal to the one or more ultrasound transducers 308 to instruct them to transmit ultrasound for ultrasonic needle localization.

Figure 5:
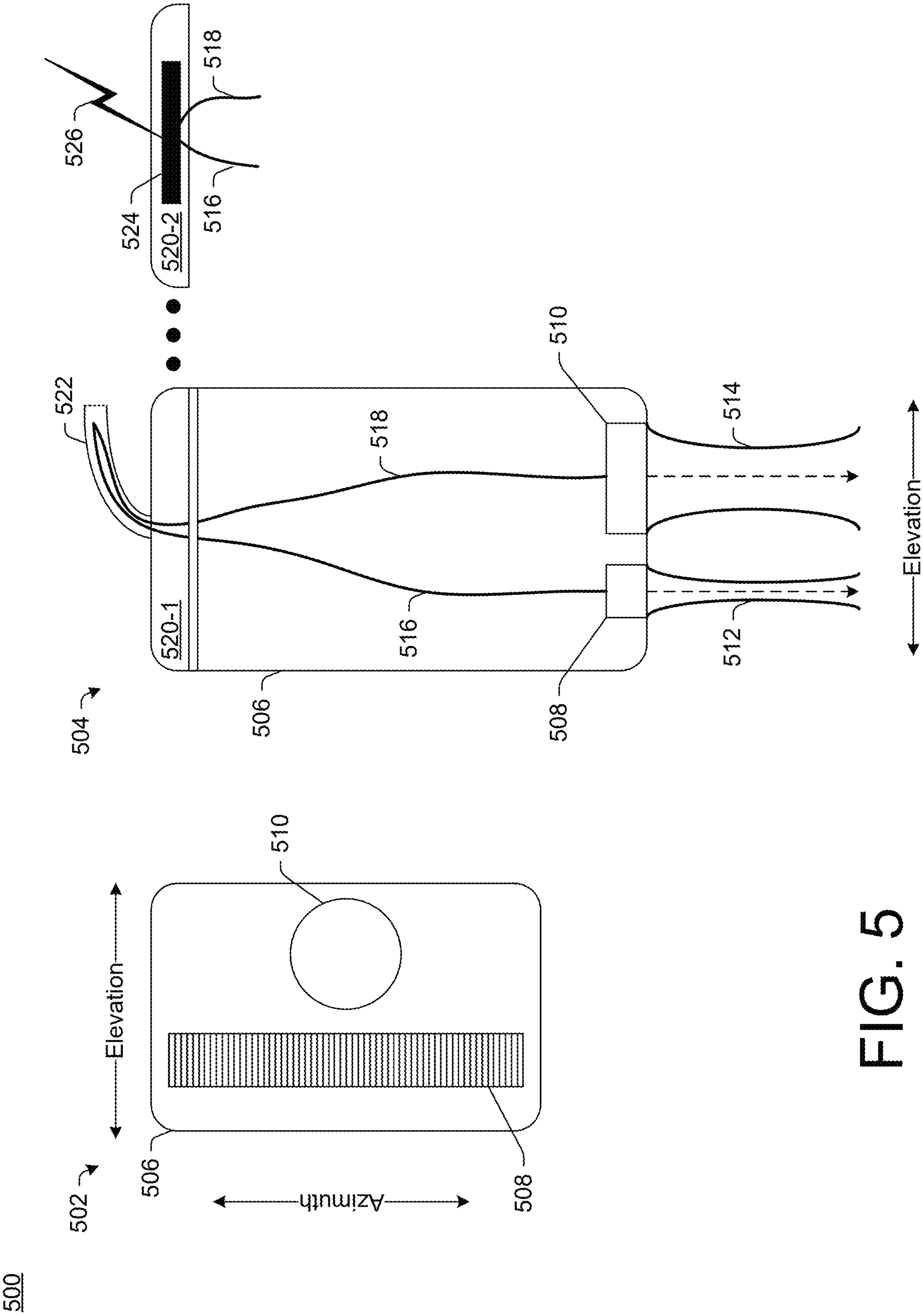
FIG. 5 illustrates a multi-array scanner for ultrasonic needle localization in accordance with some embodiments.

FIG. 5 illustrates a multi-array scanner 500 for ultrasonic needle localization in accordance with some embodiments. Generally, a multi-array scanner in accordance with some embodiments can include any suitable type and number of arrays that can be used for ultrasonic needle localization (including detection, tracking, visualization, and guidance). For instance, a multi-array scanner in accordance with some embodiments can include one or more of the arrays described in U.S. patent application Ser. No. 18/613,694, filed on Mar. 22, 2024, and entitled "Multi-Dimensional and Multi-Frequency Ultrasound Transducers" to Zhang et al., the disclosure of which is incorporated herein by reference in its entirety. Further, a multi-array scanner in accordance with some embodiments can include one or more of the arrays described in U.S. patent application Ser. No. 17/561,313, filed on Dec. 23, 2021, and entitled "Array Architecture and Interconnection for Transducers" to Li et al., the disclosure of which is incorporated herein by reference in its entirety.

The multi-array scanner 500 illustrated in FIG. 5 is illustrated with an end view 502 of the scanner and a side view 504 of the scanner. The multi-array scanner 500 includes a housing 506 that encloses a first transducer array 508 and a second transducer array 510. In some embodiments, the second transducer array 510 is a single-element transducer. The system can use the single-element transducer for needle localization, rather than imaging of a patient anatomy. In some embodiments, the second transducer array 510 can receive ultrasound transmitted by the transducer 308 on the needle 306 previously described. Additionally or alternatively, the second transducer array 510 can transmit ultrasound that can be received by the transducer 308 on the needle 306. Hence, the second transducer array 510 and the transducer 308 on the needle 306 can work together to implement ultrasonic needle localization.

In some embodiments, the system can use the first transducer array 508 for imaging of a patient anatomy. Hence, the first transducer array 508 can generate ultrasound in an imaging beam 512, and the second transducer array 510 can generate ultrasound in a needle detection beam 514. In some embodiments, the imaging beam 512 and the needle detection beam 514 have beam axes that are parallel to each other. The first transducer array 508 and the second transducer array 510 can operate at the same or different frequencies. In some embodiments, the system sets the ultrasound frequencies used by the first transducer array 508 and the second transducer array 510 to have a ratio that is an irrational number, to reduce interference between the two channels, e.g., due to intermodulation or other nonlinearities. In some embodiments, the system sets the ultrasound frequencies used by the first transducer array 508 and the second transducer array 510 to have a ratio that is a rational number. In some other embodiments, the system sets the ultrasound frequencies used by the second transducer array 510 outside the bandwidth of the first transducer array 508.

In some embodiments, the first transducer array 508 is coupled to an interconnect 516, and the second transducer array 510 is coupled to an interconnect 518. The interconnects 516 and 518 can include wires, cables, flex circuits, traces, and the like to provide signals to the first transducer array 508 and the second transducer array 510, such as transmit waveforms, as well as to transfer signals from the first transducer array 508 and the second transducer array 510, such as ultrasound signals received from the first transducer array 508 and the second transducer array 510.

In some embodiments, the multi-array scanner 500 illustrated via the side view 504 is implemented with a removably attachable proximal end portion 520-1 or 520-2. For instance, the end portions 520-1 and 520-2 can be removed from, and attached to the housing 506, one at a time. The end portion 520-1 facilitates a wired use of the multi-array scanner 500. Hence, the interconnects 516 and 518 are coupled via the end portion 520-1 to a scanner cable 522 that can be connected to an ultrasound machine. The end portion 520-2 facilitates a wireless use of the multi-array scanner 500. As such, the end portion 520-2 includes wireless transceiver electronics 524, such as one or more integrated circuits, that can transfer data between a wireless communication link 526 and the interconnects 516 and 518. The wireless communication link 526 can transfer data between the multi-array scanner 500 and another device, such as an ultrasound machine and/or a medical archiver.

Figure 6:
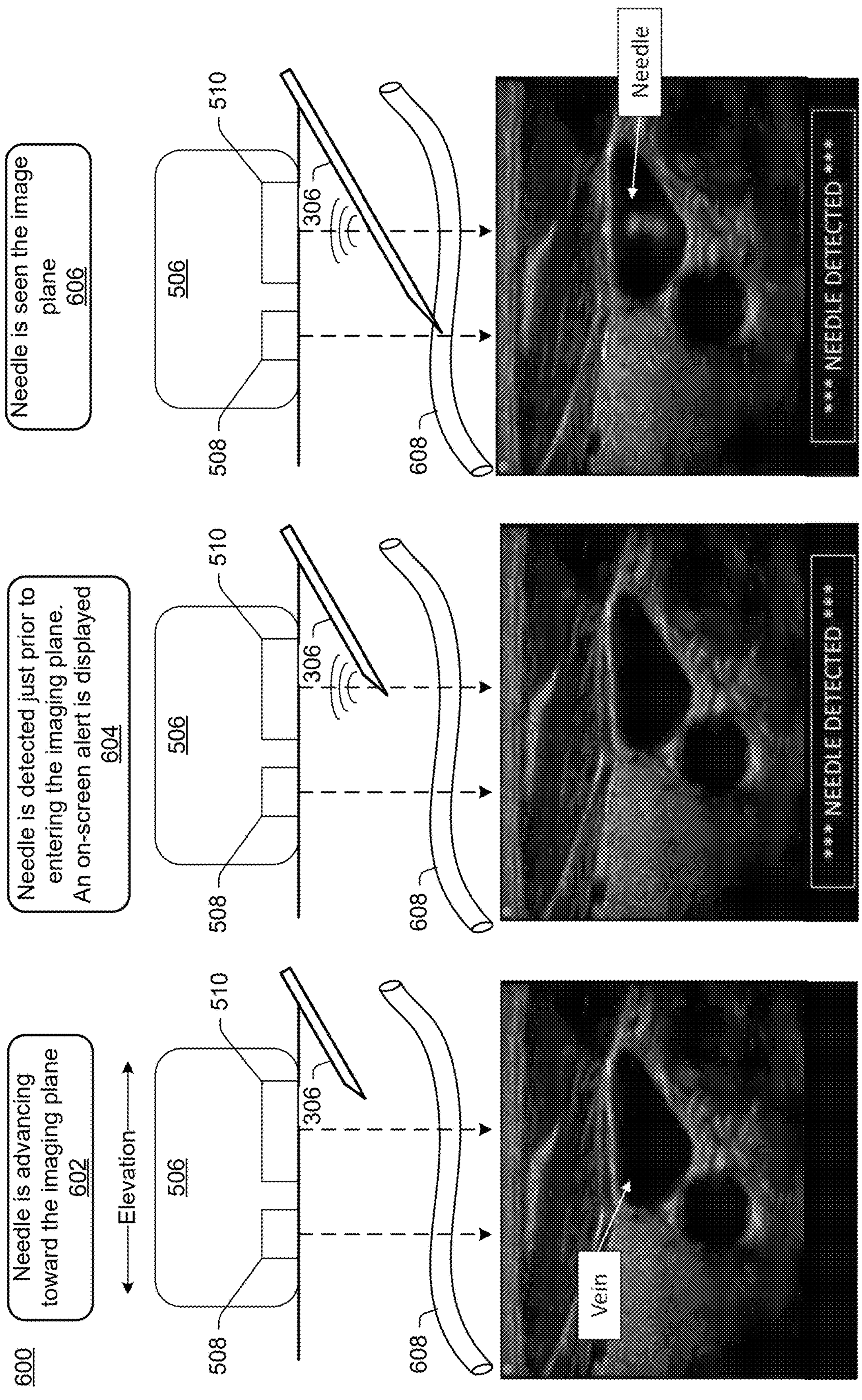
FIG. 6 illustrates ultrasonic needle localization with a multi-array scanner in accordance with some embodiments.

FIG. 6 illustrates an environment 600 for ultrasonic needle localization with a multi-array scanner, such as the multi-array scanner 500, in accordance with some embodiments. The environment 600 depicts three phases of some embodiments of a needle insertion procedure, including a first phase 602, a second phase 604, and a third phase 606.

During the first phase 602, a needle 306 is advancing towards the imaging plane and ultrasound beam of the first transducer array 508 for insertion into a vein 608. The imaging plane is displayed in a B-mode image in which the vein 608 is visible (and the needle 306 is not yet visible). The system has not yet detected the needle 306 since it has not yet crossed the ultrasound beam generated from the second transducer array 510 (which in this example is dedicated to needle detection).

During the second phase 604, the needle 306 is detected just prior to entering the imaging plane, since the needle has now crossed the ultrasound beam generated from the second transducer array 510. In response to the second transducer array 510 detecting the needle 306, the system displays an on-screen alert "Needle Detected", by overlaying the alert on the B-mode image.

During the third phase 606, the needle 306 is in the imaging plane of the first transducer array 508 and is still crossing the ultrasound beam generated from the second transducer array 510. Hence, the system continues to display the on-screen alert, and the needle 306 is visible in the B-mode image.

Note that for the process in FIG. 6, the housing 506 is placed so the needle 306 is encountered by the ultrasound beam from the second transducer array 510 before the ultrasound beam from the first transducer array 508.

The on-screen alert "Needle Detected" is an example of a binary indicator that can be generated and displayed by the system to alert the user that the system has detected the needle 306. Other examples of binary indicators that the system can display include an icon (e.g., a thumbs-up icon to indicate needle detection and a thumbs-down icon to indicate the needle has not yet been detected), a color coding (e.g., changing the color of a visual representation from red to green to indicate that the needle has been detected), an animation, a number, a check mark, etc. By displaying a visual representation comprising a binary indicator, the user can quickly, easily, and unambiguously determine whether or not a needle has been detected. In contrast, when using conventional ultrasound systems that merely rely on the presence or absence of the needle in the B-mode image for indication of needle detection, the user can be confused and unsure as to whether or not the needle has been detected, due to poor imaging quality, angle of insertion, etc.

In some embodiments, the system can display an on-screen alert to indicate the needle insertion that is not a binary indicator. For instance, the system can display a grade, e.g., a number between 1 and 5, to indicate a confidence that the needle is detected. In some other embodiments, the system can display a number that indicates an amount of insertion, such as a length of the needle that is inserted into the patient, a percentage of the total needle length that is inserted, a remaining distance from the needle tip to the vein 608, and the like.

In some embodiments, the system can perform a calibration routine prior to performing a needle insertion procedure. In some embodiments, the calibration routine determines a baseline signal measured by one or more of the arrays, such as the second transducer array 510 used for detecting the needle and then removes (e.g., subtracts) the baseline signal from the signal measured by the second transducer array 510 during the needle procedure, to improve needle detection accuracy. During calibration, the scanner position and angle can be adjusted to obtain the baseline signal from different regions of the anatomy so that the variation in baseline data (e.g., RF data) can be determined, and used to further improve needle detection accuracy.

Figure 7:
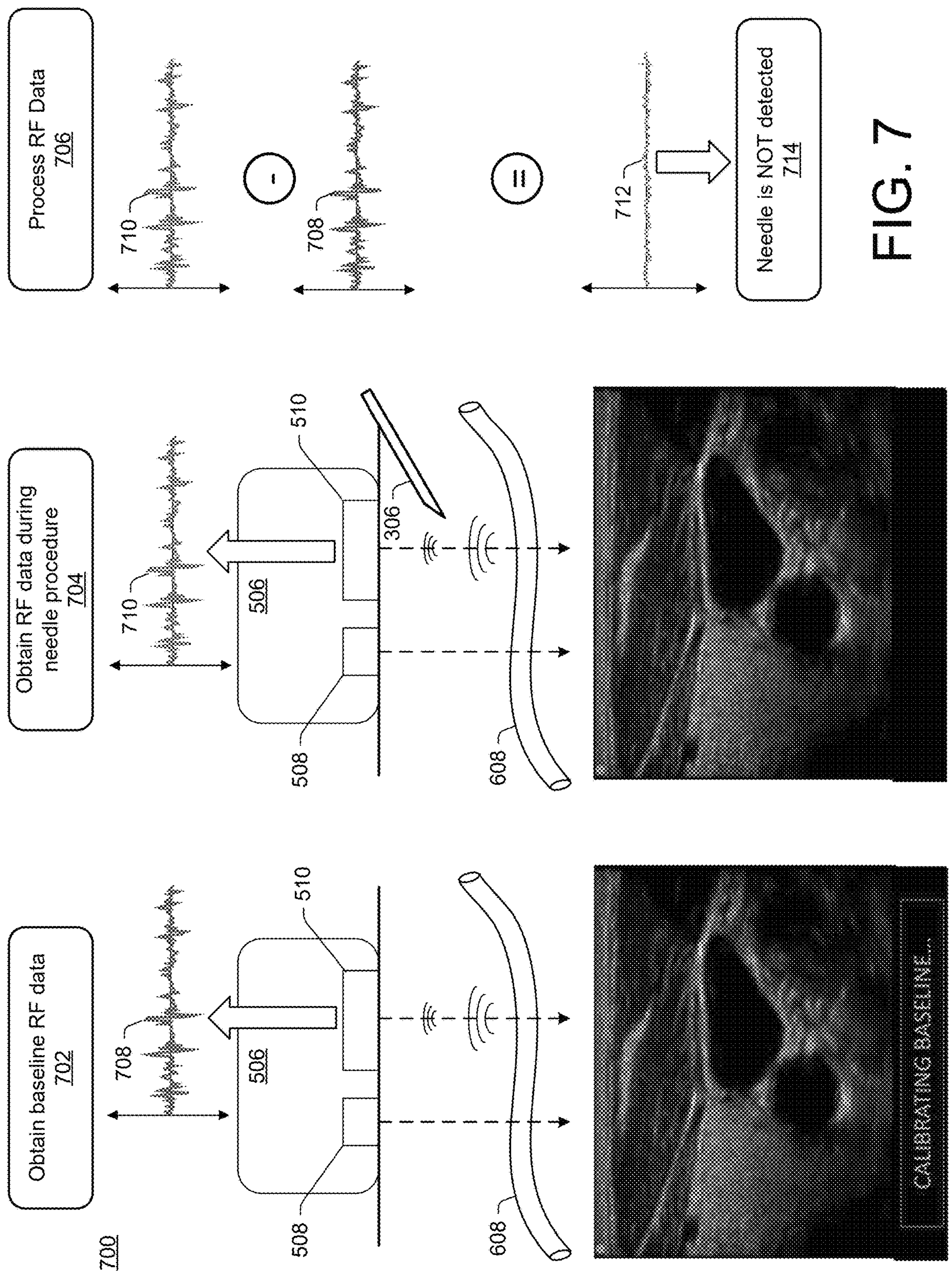
FIG. 7 illustrates an example of baseline data for ultrasonic needle localization in accordance with some embodiments.
Figure 8:
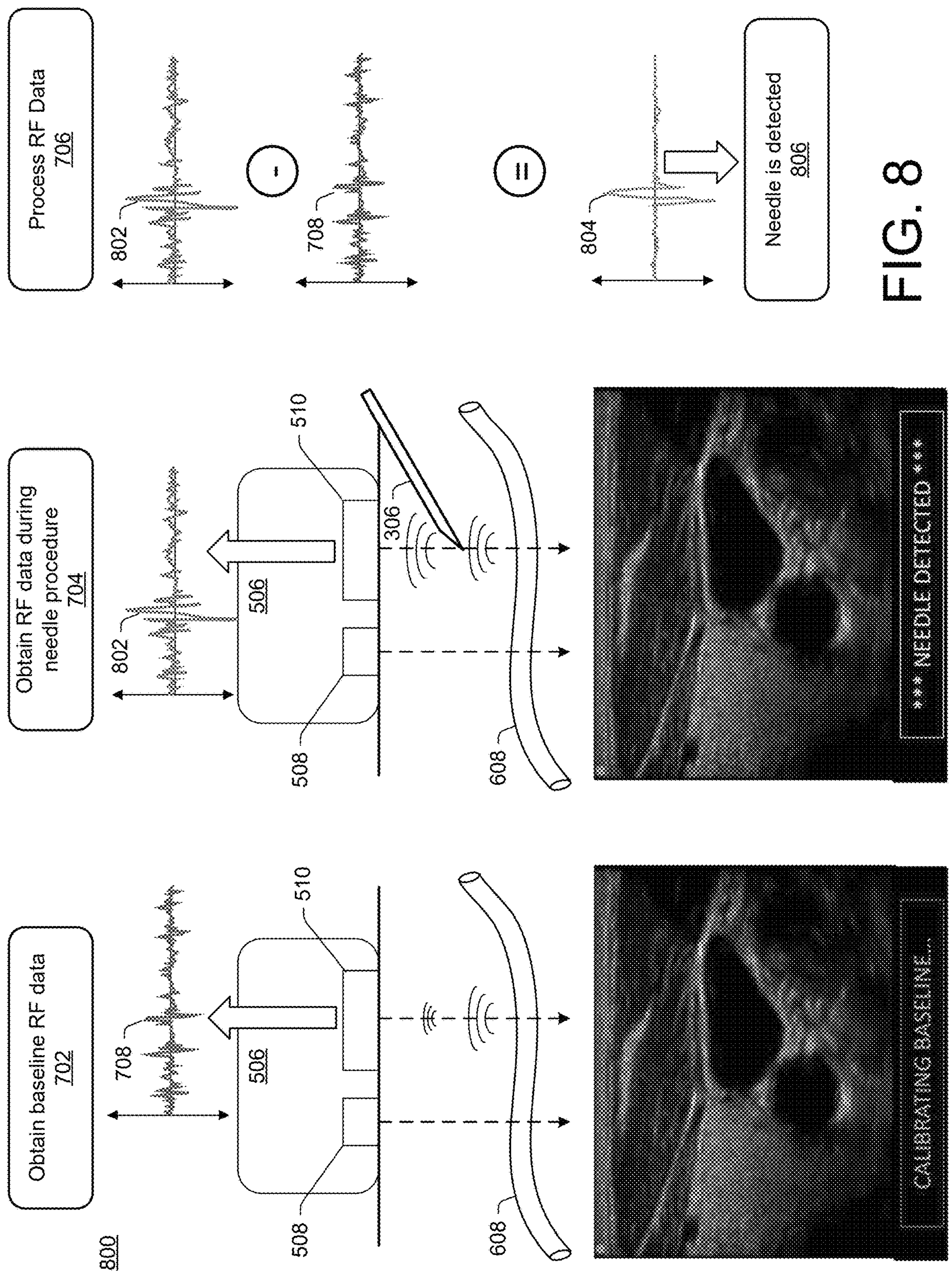
FIG. 8 illustrates an example of calibration of baseline data for ultrasonic needle localization in accordance with some embodiments.

FIG. 7 depicts the calibration 700 of baseline data when a needle is not detected, and FIG. 8 depicts the calibration 800 of baseline data when a needle is detected. Both FIG. 7 and FIG. 8 depict three phases of the calibration routine and use, including a first phase 702 in which baseline RF data is obtained, a second phase 704 in which RF data during a needle procedure is obtained, and a third phase 706 in which the RF data is processed to determine whether a needle has been detected.

Referring to FIG. 7, at the first phase 702, baseline RF data 708 is obtained by the second transducer array 510 prior to a needle insertion procedure. The system can store the baseline RF data 708 in memory for subsequent use (e.g., for use during the needle insertion procedure). During this phase, the system displays the alert "Calibrating Baseline" on the user interface, e.g., overlaid on the B-mode image. At the second phase 704, RF data 710 is obtained by the second transducer array 510 during the needle insertion procedure, but before the needle 306 crosses the ultrasound beam generated by the second transducer array 510. At the third phase, the system retrieves the baseline RF data 708 from memory and removes it (e.g., subtracts it) from the RF data 710 to generate the waveform 712. Based on the waveform 712, e.g., a lack of a peak or energy in the waveform 712, the system declares at 714 that the needle 306 is not detected.

In FIG. 8, the second phase 704 is repeated and RF data 802 is obtained by the second transducer array 510 during the needle insertion procedure and while the needle 306 crosses the ultrasound beam generated by the second transducer array 510. At the third phase, the system retrieves the baseline RF data 708 from memory and removes it (e.g., subtracts it) from the RF data 802 to generate the waveform 804. Based on the waveform 804, e.g., a peak or energy in the waveform 804, the system declares at 806 that the needle 306 is detected and displays the alert "Needle Detected" on the B-mode image. Note that the determination that the needle 306 is detected is more robust by using the waveform 804 (after calibration) compared to using the RF data 802 (prior to calibration), due to the noise on the RF data 802. Further, subtraction of the baseline RF data is one method the system can use to remove it from the RF data. Other examples include filtering, deconvolution, division, etc.

While FIG. 7 and FIG. 8 illustrate needle detection in the time domain, the process of needle detection could be done in the frequency domain as part of a frequency domain analysis. The frequency domain analysis could involve component analysis and/or the use of filtering to remove baseline components in the baseline from the obtained RF signals related to the detected object. In such a case, a pulse inversion approach can be used. Alternatively, an acoustic signature or other pattern indicative of the presence of a needle can be created and used to identify the presence of a needle when an object is identified in the received RF signals that matches that signature or pattern. The determination of a match can be based on a threshold (e.g., the object matches some percentage (e.g., 95%) of the signature or pattern).

In some embodiments, a scanner in accordance with some embodiments, such as the scanner 104 or the multi-array scanner 500, can use variable elevational planes for ultrasonic needle localization. Based on the width of the elevational beam, there can be uncertainty about the needle tip location. For instance, for higher frequency ultrasound, the thickness of the elevational beam can be narrow compared to that when a lower frequency ultrasound is used. Hence, with higher frequency ultrasound (and the resulting narrow elevational beam), the needle may not be detected, whereas with lower frequency ultrasound (and the resulting wider elevational beam), the needle may be detected. FIG. 9 illustrates a system 900 that takes advantage of this observation by interleaving variable elevational planes for ultrasonic needle localization in accordance with some embodiments.

Figure 9:
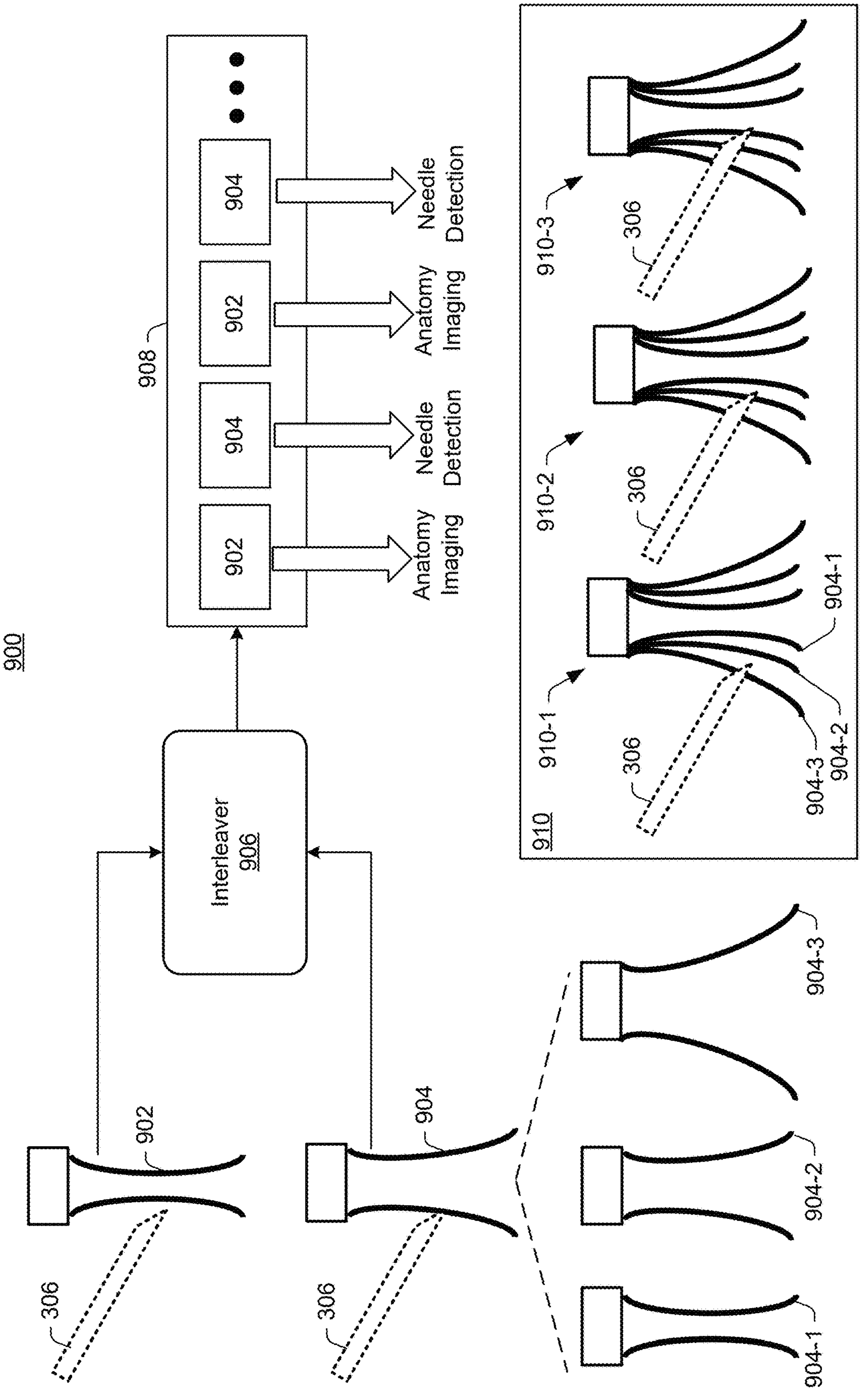
FIG. 9 illustrates interleaving of variable elevational planes for ultrasonic needle localization in accordance with some embodiments.

Referring to FIG. 9, the system 900 includes a first elevational beam 902 and a second elevational beam 904. The first elevational beam 902 can be generated by higher frequency ultrasound than the second elevational beam 904, and therefore the first elevational beam 902 is narrower than the second elevational beam 904. Hence, the needle 306 at the position in FIG. 9 may not be detected by the first elevational beam 902. However, at the same position, the needle 306 does intersect the second elevational beam 904 and can therefore be detected by the second elevational beam 904. The system 900 therefore includes an interleaver 906 that generates a sequence 908 that interleaves ultrasound pings having a high frequency (and thus having the thickness of the first elevational beam 902) with ultrasound pings having a low frequency (and thus having the thickness of the second elevational beam 904). The system 900 uses the pings of the sequence 908 having the first elevational beam 902 for anatomy imaging (e.g., for generating a B-mode image), and uses the pings of the sequence 908 having the second elevational beam 904 for localizing the needle 306. The first elevational beam 902 and the second elevational beam 904 can be generated by a same transducer array of a scanner 104, or different transducer arrays of a multi-array scanner, such as the multi-array scanner 500.

In some embodiments, the system 900 uses multiple lower frequencies to interleave elevational beams of various widths for needle localization with a narrow elevational beam (due to a higher ultrasound frequency) for imaging of the patient anatomy. For example, the system 900 includes multiple elevational beams 904-1, 904-2, and 904-3, which are examples of the second elevational beam 904. The elevational beam 904-1 can be generated with a first frequency $f_1$, the elevational beam 904-2 can be generated with a second frequency $f_2$, and the elevational beam 904-3 can be generated with a third frequency $f_3$, where $f_1>f_2>f_3$. For example, in some embodiments, $f_1$ is 15 MHz, $f_2$ is 10 MHz and $f_3$ is 8 MHz, though other frequencies can be used. In some embodiments, a range of 4-6 MHz is used for the transducer(s) being used for needle detection.

To interleave the elevational beams 904-1, 904-2, and 904-3 with the first elevational beam 902, the system 900 can selects one of the elevational beams 904-1, 904-2, and 904-3 every other sample (and the first elevational beam 902 when not selecting one of the elevational beams 904-1, 904-2, and 904-3). The system can cycle through the elevational beams 904-1, 904-2, and 904-3 in order, and then repeat, e.g., 904-1 followed by 904-2 followed by 904-3, and then repeat with 904-1. As the needle 306 is inserted into the patient, the system 900 can track the motion of the needle 306, e.g., by tracking the position of the needle tip with the elevational beams 904-1, 904-2, and 904-3.

For example, inset 910 illustrates three views 910-1, 910-2, and 910-3 as the needle 306 is inserted. At view 910-1, the tip of the needle 306 is detected by the elevational beam 904-3 generated with ultrasound frequency $f_3$, because the needle tip intersects the elevational beam 904-3. However, the needle 306 is not detected by the elevational beam 904-1 generated with ultrasound frequency $f_1$ or the elevational beam 904-2 generated with ultrasound frequency $f_2$, as the needle does not intersect the elevational beams 904-1 and 904-2. At view 910-2, the tip of the needle 306 is detected by the elevational beam 904-2 generated with ultrasound frequency $f_2$ and the elevational beam 904-3 generated with ultrasound frequency $f_3$, because the needle tip intersects both the elevational beams 904-2 and 904-3. However, the needle 306 is not detected by the elevational beam 904-1 generated with ultrasound frequency $f_1$ as the needle does not intersect the elevational beam 904-1. At view 910-3, the tip of the needle 306 is detected by all three of the elevational beams 904-1, 904-2, and 904-3, because the needle tip intersects each of these elevational beams.

Based on the detection of the needle 306 over time by the elevational beams 904-1, 904-2, and 904-3, the system 900 can determine a trajectory of the needle tip. For instance, the system 900 can connect the intersection points of the elevational beams 904-1, 904-2, and 904-3 to generate a piece-wise linear path. In some embodiments, the system 900 smooths the piece-wise linear trajectory, e.g., with a smoothing filter, interpolator, etc. The system 900 can project the trajectory onto a plane, such as a B-mode imaging plane, A-mode plane, C-mode plane, etc., and display the trajectory via a user interface, such as by overlaying the trajectory onto an ultrasound image. The use of three elevational beams 904-1, 904-2, and 904-3 is exemplary, and the system can use any suitable number of elevational beams of various widths for needle localization, including to generate a trajectory of the needle tip.

The system can also use a multi-array scanner and generate elevational beams of different widths with the different arrays, e.g., simultaneously. One or more of the elevational beams having a narrower width (e.g., because they are generated with a high frequency ultrasound) can be used to image the patient anatomy, while one or more others of the elevational beams having a wider width (e.g., because they are generated with a low frequency ultrasound) can be used for needle localization, e.g., to detect and track the needle 306.

Figure 10:
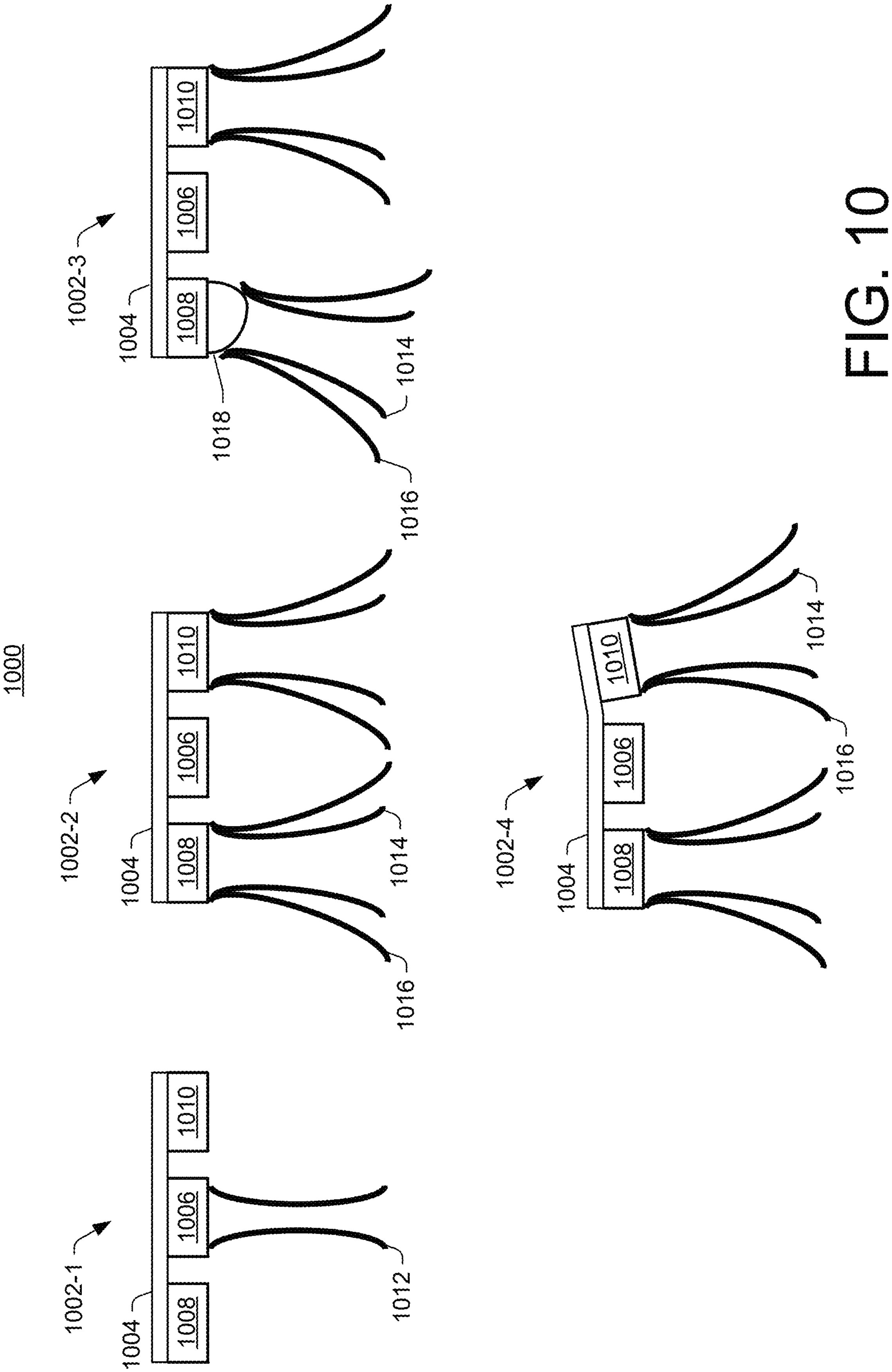
FIG. 10 illustrates variable elevational planes in a multi-array scanner for ultrasonic needle localization in accordance with some embodiments.

FIG. 10 illustrates a diagram 1000 that depicts variable elevational planes in a multi-array scanner for ultrasonic needle localization in accordance with some embodiments. The diagram includes four views 1002-1, 1002-2, 1002-3, and 1002-4 of a multi-array scanner. In each of these views, the multi-array scanner includes a substrate 1004 to which three arrays are attached, a center array 1006, a left array 1008, and a right array 1010. The arrays 1006, 1008, and 1010 can be arranged in any suitable configuration, such as in parallel rows. Further, the scanner can include any suitable number of arrays, and three is used in FIG. 10 as an example. The arrays can be arranged in a symmetric fashion (e.g., about the center array 1006), or asymmetrically (e.g., with a different number of arrays to the left of the center array 1006 than to the right of the center array 1006). In the embodiment illustrated in FIG. 10, the center array 1006 operates at a first frequency $f_{center}$, and the left array 1008 and the right array 1010 operate at one or more second frequencies $f_{side}$, with $f_{center}>f_{side}$. In some other embodiments, the left array 1008 and the right array 1010 operate at different frequencies from each other, and these frequencies can be higher or lower than the frequency used by the center array 1006.

In some embodiments, the system uses the center array 1006 for imaging of the patient anatomy, such as to generate a B-mode image, and the left array 1008 and the right array 1010 for localization (including detection, tracking, and visualization) of the needle. Because the multi-array scanner includes physically split apertures, the system can detect the needle sooner than a scanner with a single array that interleaves variable elevational planes, such as in the example described with respect to FIG. 9. In some embodiments, the system uses the center array 1006 for imaging of the patient anatomy and in-plane needle visualization and uses the outer arrays (the left array 1008 and the right array 1010) to detect if needle has left the imaging plane. The system can use several waveforms on the outer arrays to provide information on how far away from the imaging plane the needle has travelled. In some embodiments, the system can display an on-screen alert to indicate when the needle leaves the imaging plane, such as text, an icon, etc.

At view 1002-1, the center array 1006 generates a narrow elevational beam 1012 based on frequency $f_{center}$. At view 1002-2, the left array 1008 and the right array 1010 generate one of wider elevational beams 1014 and 1016 for needle localization based on frequencies $f_{side}$. Two elevational beams 1014 and 1016 of two frequencies $f_{side}$ are used in FIG. 10 as an example, and is not meant to be limiting. For instance, three, four, five, or any suitable number of frequencies can be used to generate elevational beams from the left array 1008 and the right array 1010.

In some embodiments, the system alternates between elevational beams 1014 and 1016. For instance, at one interval, each of the left array 1008 and the right array 1010 generate elevational beams 1014, and at the next interval, each of the left array 1008 and the right array 1010 generate elevational beams 1016. At the subsequent interval, the left array 1008 and the right array 1010 can again generate elevational beams 1014, and the alternating between elevational beams 1014 and 1016 can continue. Thus, the system can track the needle using the variable thicknesses of the elevational beams generated by the left array 1008 and the right array 1010 over time.

At view 1002-3, the multi-array transducer includes a lens 1018 over the left array 1008. The multi-array transducer can include any suitable lens over one or more of the center array 1006, the left array 1008, and the right array 1010. The lens 1018 is illustrated over the left array 1008 as an example and is not meant to be limiting. By steering the elevational beams 1014 and 1016 with the lens 1018, the system can provide earlier needle detection compared to a system that does not steer the elevational beams. In some embodiments, the lens 1018 is removably attached to the scanner 104. For example, the system can provide multiple lenses for use with different steering angles, and the user can select one of the lenses, e.g., the lens 1018, and attach it to one or more of the arrays, such as the left array 1008. Hence, the scanner can be a general purpose scanner that is not specific to needle detection, as could be the case if the lens 1018 is permanently attached to the scanner.

At view 1002-4, the multi-array transducer includes a substrate 1004 that is bent/deformed from being flat, and thereby positions the right array 1010 at an angle (e.g., relative to the other arrays 1006 and 1008) to steer the elevational beams 1014 and 1016. The substrate 1004 can be permanently bent/deformed, or temporarily bent/deformed. For instance, the substrate 1004 can be rigid, semi-rigid, or flexible. In some embodiments, the substrate 1004 returns to its original shape after it is bent/deformed. In some other embodiments, the substrate 1004 retains its bent position after it is bent/deformed. Accordingly, the deformable substrate 1004 in the view 1002-4 is suitable for wearable ultrasound devices, such as the wristband 104-3 and the patch 104-4 previously described.

In some embodiments, one or more of the elevational beams can be tilted inward to facilitate the needle detection. The tilting of the beam(s) can be accomplished through the use of a concave and/or convex lens. Alternatively, the tilting of the beam(s) can be accomplished by bending the substrate containing a portion of the transducer array. Thus, using different transmit waveforms and lens steering angles can facilitate a needle detection process. In such a case, if the transmit waveform is solely used for imaging, a lower frequency (e.g., 4-6 MHz, etc.) can be used.

An Example User Interface

Figure 11:
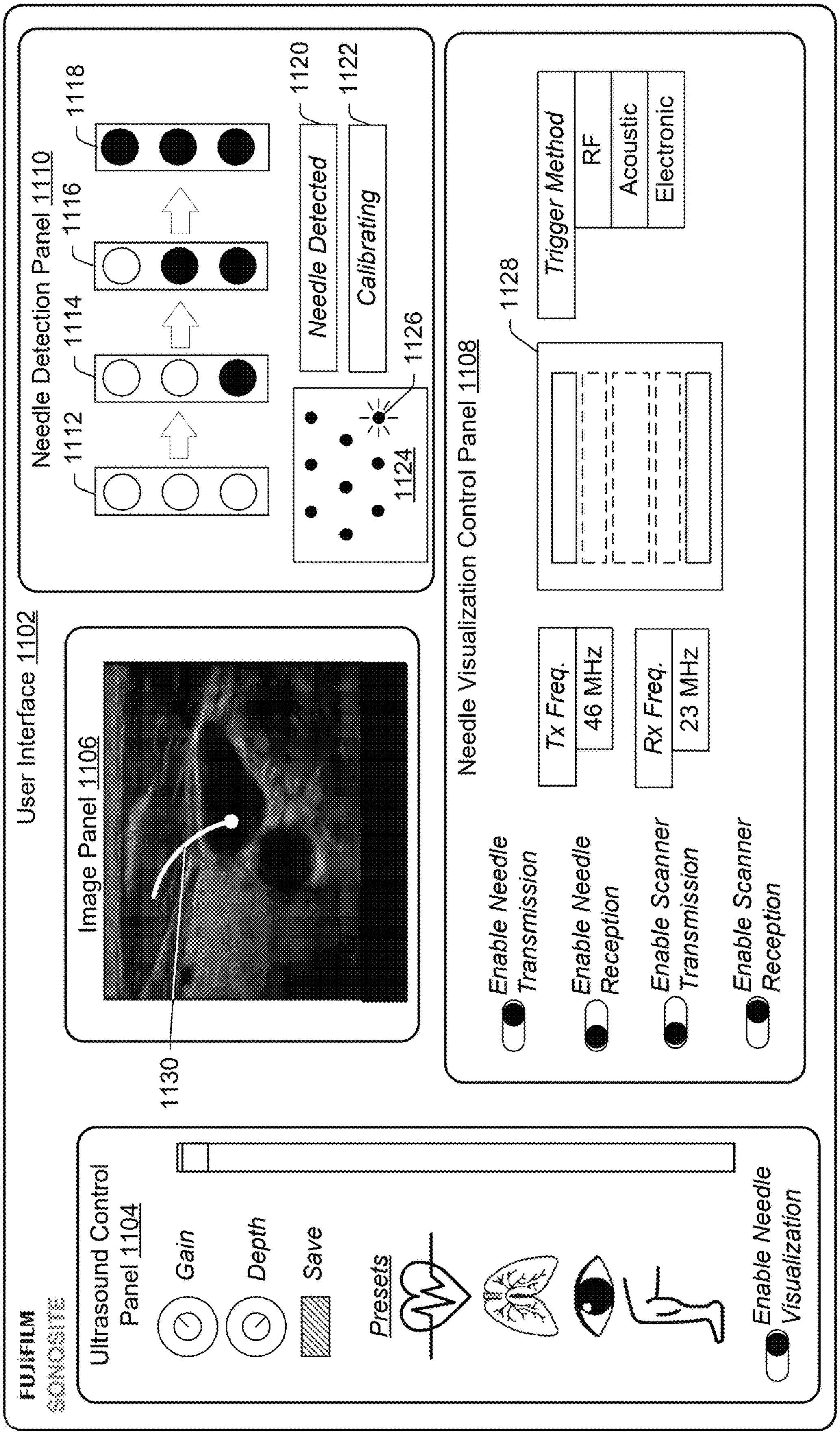
FIG. 11 illustrates a user interface for ultrasonic needle localization in accordance with some embodiments.

FIG. 11 illustrates an example user interface 1102 of an ultrasound system for ultrasonic needle localization in accordance with some embodiments. The user interface 1102 can be displayed via an ultrasound machine (e.g., the ultrasound machine 102), and/or a display device (e.g., the display device 108). In some embodiments, the user interface 1102 includes an ultrasound control panel 1104, an image panel 1106, a needle visualization control panel 1108, and a needle detection panel 1110.

In some embodiments, the ultrasound control panel 1104 includes any suitable controls and settings for controlling an ultrasound system, such as depth and gain adjustments, and a button to store images and/or video clips. The ultrasound control panel 1104 can also include icons to select examination presets, such as a heart icon for a cardiac preset, a lung icon for a respiratory preset, an eye icon for an ocular present, and a leg icon for a muscular-skeletal preset. The ultrasound control panel 1104 can also include options (not shown for clarity) to enable one or more neural networks for processing of an ultrasound image, such as an ultrasound image displayed in the image panel 1106. For instance, a cardiac neural network can be enabled to generate a value of ejection fraction, a free fluid network can be enabled to generate a segmentation of free fluid in an ultrasound image, and a pneumothorax (PTX) neural network can be enabled to generate a probability of a pneumothorax condition or collapsed lung.

In some embodiments, the image panel 1106 can display any suitable ultrasound image, such as a B-mode image, M-mode image, Doppler image, etc. The image panel 1106 can also display a measurement, annotation, classification, and the like. For instance, a trajectory 1130 of a needle tip is illustrated in the image panel 1106 in FIG. 11. The trajectory 1130 includes a circle at one end to indicate a current position of the needle tip. In some embodiments, the image panel 1106 can display an inference generated by a neural network, such as a segmentation of the blood vessel in the B-mode image in FIG. 11.

In some embodiments, the needle visualization control panel 1108 can display any suitable data and selections for configuring ultrasonic needle localization in accordance with some embodiments. In the example in FIG. 11, the needle visualization control panel 1108 includes a binary switch (e.g., with on and off positions) to enable and disable needle transmission, e.g., with the ultrasound transducers 308 on the tip of a needle. The needle visualization control panel 1108 also includes a binary switch to enable and disable needle reception, e.g., with the ultrasound transducers 308 on the tip of a needle. The needle visualization control panel 1108 also includes a binary switch to enable and disable scanner transmission for needle visualization, e.g., with the ultrasound array 302. The needle visualization control panel 1108 also includes a binary switch to enable and disable scanner reception for needle localization, e.g., with the ultrasound array 302.

The needle visualization control panel 1108 also includes options, e.g., drop-down tabs, to set one or more transmission frequencies. Based on the settings of the binary switches in the needle visualization control panel 1108, the transmission frequency can correspond to the ultrasound transducers 308 or the ultrasound array 302. In FIG. 11, the transmission frequency of ultrasound is set to 46 MHz. The needle visualization control panel 1108 also includes options, e.g., drop-down tabs, to set one or more reception frequencies. Based on the settings of the binary switches in the needle visualization control panel 1108, the reception frequency can correspond to the ultrasound transducers 308 or the ultrasound array 302. In FIG. 11, the reception frequency of ultrasound is set to 23 MHz in accordance with some embodiments. Hence, since the reception frequency is set to half the transmission frequency, the system is configured for subharmonic detection. Note that the techniques disclosed herein are not limited to using a reception frequency of ultrasound being set to 23 MHz.

In some embodiments, the needle visualization control panel 1108 also includes an option to configure a multi-array scanner for ultrasonic needle visualization. The visual representation 1128 includes a graphic of a five-row array, having a center row array and two outer row arrays symmetrically arranged on each side of the center row array. A user can select the arrays (e.g., via a touch or cursor click) to enable/disable the rows for needle detection. In the example in FIG. 11, the user has selected the two outer-most array rows for needle detection (as evidenced by their solid line depictions). The user has also not selected (or disabled) the center array and adjacent arrays to the center array for needle detection, as evidenced by their dashed line depictions. The needle visualization control panel 1108 can include options for setting frequencies of the array rows (not shown for clarity). For instance, a user may double click on an array row of the visual representation 1128 to open a frequency box for the row, and enter a suitable frequency in the frequency box. Alternatively, the frequencies of the multi-row array can be set via the drop-down tabs displayed in the needle visualization control panel 1108.

In some embodiments, the needle visualization control panel 1108 also includes a drop-down menu to select a method to trigger an ultrasonic transducer for needle detection, such as the ultrasound transducers 308 on the tip of the needle 306. For instance, a user can select from RF, acoustic, and electronic wake-up options to trigger the ultrasound transducers 308 to start transmitting and/or receiving ultrasound for ultrasonic needle localization, such as described with respect to FIG. 3.

The needle detection panel 1110 can display any suitable results generated or obtained by the ultrasound system during a needle insertion procedure. In the example in FIG. 11, the needle visualization control panel 1108 can display any one of four columns of three lights, lights 1112-1118. Based on the detection of the needle, the needle visualization control panel 1108 can display one of these columns of lights. The detection can be based on any one or more of the detection methods disclosed herein, including whether or not a needle is detected by a transducer array, such as the first transducer array 508, second transducer array 510, or the ultrasound arrays 302. For instance, with regards to FIG. 6, if the system at the first phase 602 does not detect the needle 306, then the needle detection panel 1110 can display the column 1112, with no lights activated. However, if the system at the second phase 604 detects the needle 306 with the second transducer array 510 but not with the first transducer array 508, then the needle detection panel 1110 can display the column 1114, with only one of three lights activated. Further, if the system at the third phase 606 detects the needle 306 with both the second transducer array 510 and the first transducer array 508, then the needle detection panel 1110 can display one of the columns 1116 or 1118, with multiple of three lights activated.

In some embodiments, the system can display one of the columns of lights 1112-1118 based on the detection as illustrated at inset 910 in FIG. 9. For example, if the needle is not detected by any of the elevational beams, then the needle detection panel 1110 can display the column 1112, with no lights activated. However, if as illustrated at view 910-1 that one of the elevational beams detects the needle, then the needle detection panel 1110 can display the column 1114, with only one of three lights activated. When two of the elevational beams detect the needle as is depicted at view 910-2, then the needle detection panel 1110 can display the column 1116, with two of the three lights activated. When three of the elevational beams detect the needle as is depicted at view 910-3, then the needle detection panel 1110 can display the column 1118, with all three lights activated.

In some embodiments, the needle detection panel 1110 can also display any suitable alert or warning, such as the text box 1120 depicting “Needle Detected” to indicate that the system has detected an image, or the text box 1122 depicting “Calibrating” to indicate the system is performing a calibration routine to establish an RF baseline that can be removed, e.g., calibrated out, from RF data captured by the system during a needle insertion procedure, as previously described.

Further, the needle detection panel 1110 can display a visual representation 1124 of a hole pattern of a wearable ultrasound transducer, such as the wearable patch 104-4 previously described. In some embodiments, the ultrasound system implements a machine-learned model (e.g., a neural network) to generate a recommendation to use one or more of the holes in the hole pattern for needle insertions. As an example, the hole 1126 is highlighted/blinking to indicate that the ultrasound system recommends this hole for insertion of the needle.

An Example Device

Figure 12:
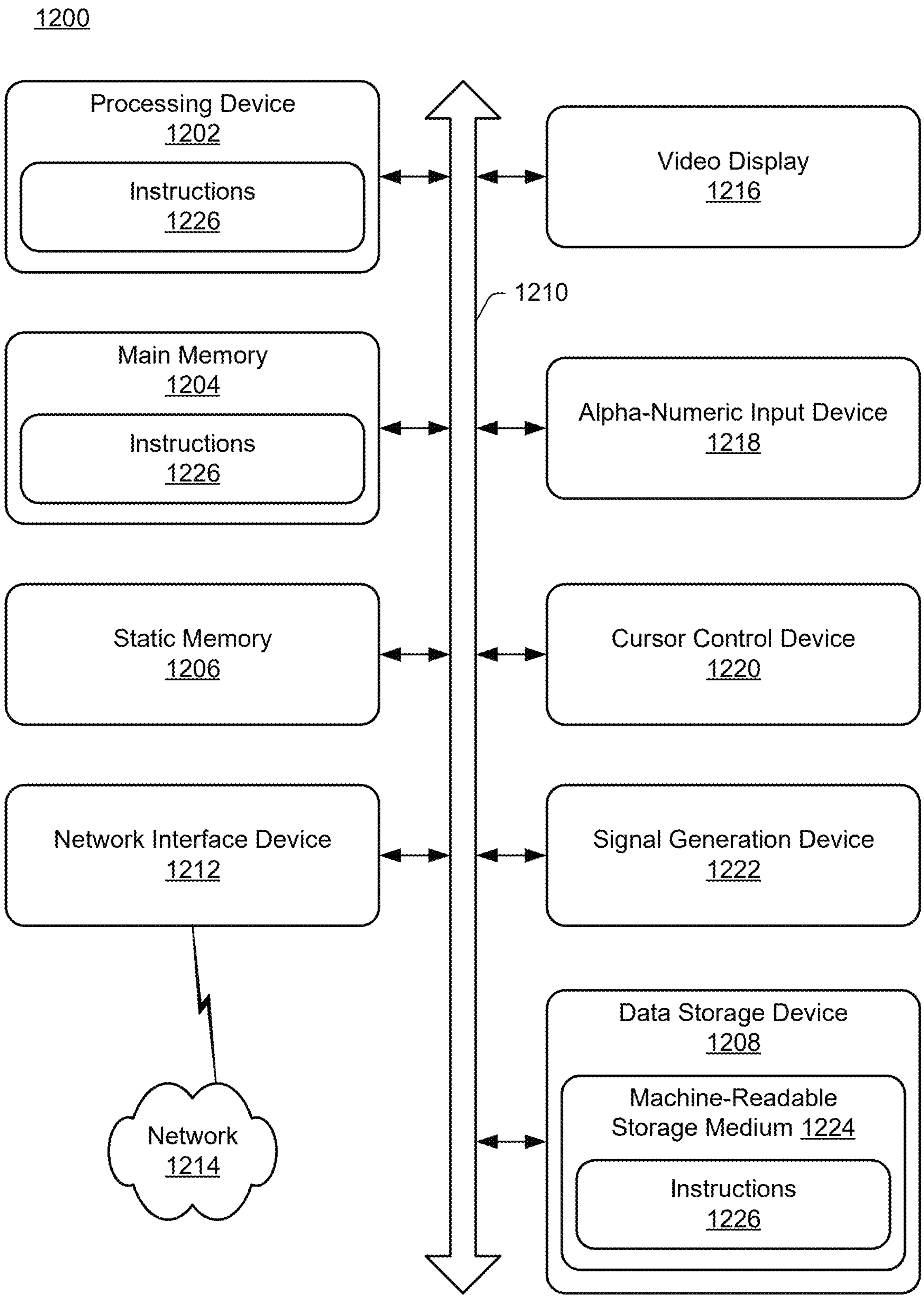
FIG. 12 illustrates an example device for ultrasonic needle localization in accordance with some embodiments.

FIG. 12 illustrates a block diagram of an example computing device 1200 that can perform one or more of the operations described herein, in accordance with some implementations. The computing device 1200 can be connected to other computing devices in a local area network (LAN), an intranet, an extranet, and/or the Internet. The computing device can operate in the capacity of a server machine in a client-server network environment or in the capacity of a client in a peer-to-peer network environment. The computing device can be provided by a personal computer (PC), a server computer, a desktop computer, a laptop computer, a tablet computer, a smartphone, an ultrasound machine, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein. In some embodiments, the computing device 1200 is one or more of an ultrasound machine, an ultrasound scanner, an access point, a charging station, and a medical archiver.

The example computing device 1200 can include a processing device 1202 (e.g., a general-purpose processor, a programmable logic device (PLD), etc.), a main memory 1204 (e.g., synchronous dynamic random-access memory (DRAM), read-only memory (ROM), etc.), and a static memory 1206 (e.g., flash memory, a data storage device 1208, etc.), which can communicate with each other via a bus 1210. The processing device 1202 can be provided by one or more general-purpose processing devices such as a microprocessor, a central processing unit, or the like. In an illustrative example, the processing device 1202 comprises a complex instruction set computing (CISC) microprocessor, a reduced instruction set computing (RISC) microprocessor, a very long instruction word (VLIW) microprocessor, or a processor implementing other instruction sets or processors implementing a combination of instruction sets. The processing device 1202 can also comprise one or more special-purpose processing devices such as an application-specific integrated circuit (ASIC), a field programmable gate array (FPGA), a digital signal processor (DSP), a network processor, or the like. The processing device 1202 can be configured to execute the operations described herein, in accordance with one or more aspects of the present disclosure, for performing the operations and steps discussed herein.

The computing device 1200 can further include a network interface device 1212, which can communicate with a network 1214. The computing device 1200 also can include a video display unit 1216 (e.g., a liquid crystal display (LCD), an organic light-emitting diode (OLED), a cathode ray tube (CRT), etc.), an alphanumeric input device 1218 (e.g., a keyboard), a cursor control device 1220 (e.g., a mouse), and an acoustic signal generation device 1222 (e.g., a speaker, a microphone, etc.). In one embodiment, the video display unit 1216, the alphanumeric input device 1218, and the cursor control device 1220 can be combined into a single component or device (e.g., an LCD touch screen).

The data storage device 1208 can include a computer-readable storage medium 1224 on which can be stored one or more sets of instructions 1226 (e.g., instructions for carrying out the operations described herein, in accordance with one or more aspects of the present disclosure). The instructions 1226 can also reside, completely or at least partially, within the main memory 1204 and/or within the processing device 1202 during execution thereof by the computing device 1200, where the main memory 1204 and the processing device 1202 also constitute computer-readable media. The instructions can further be transmitted or received over the network 1214 via the network interface device 1212.

Various techniques are described in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. In some aspects, the modules described herein are embodied in the data storage device 1208 of the computing device 1200 as executable instructions or code. Although represented as software implementations, the described modules can be implemented as any form of a control application, software application, signal-processing and control module, hardware, or firmware installed on the computing device 1200.

While the computer-readable storage medium 1224 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding, or carrying a set of instructions for execution by the machine and that causes the machine to perform the methods described herein. The term "computer-readable storage medium" shall accordingly be taken to include, but not be limited to, solid-state memories, optical media, and magnetic media.

An Example Environment

Figure 13:
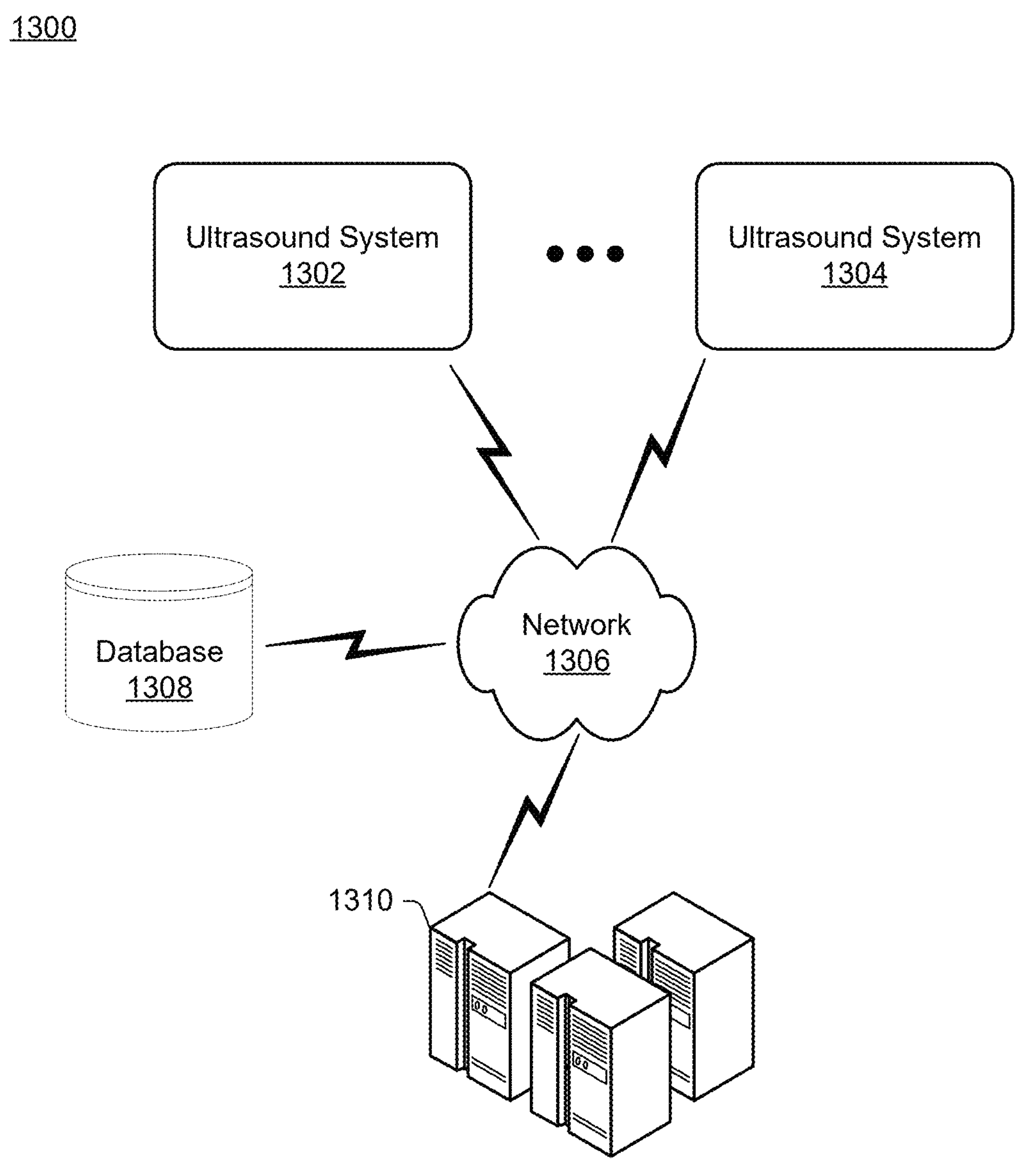
FIG. 13 illustrates an example environment for ultrasonic needle localization in accordance with some embodiments.

FIG. 13 illustrates an environment 1300 for an ultrasound system in accordance with some embodiments. The environment 1300 includes an ultrasound system 1302 and an ultrasound system 1304. Two example ultrasound systems 1302 and 1304 are illustrated in FIG. 13 for clarity. However, the environment 1300 can include any suitable number of ultrasound systems, such as the ultrasound systems maintained by a care facility or the department of a care facility. Generally, an ultrasound system can include any suitable device (e.g., a component of an ultrasound system). Examples devices of the ultrasound systems 1302 and 1304 include a charging station, an ultrasound machine, a display device (e.g., a tablet or smartphone), an ultrasound scanner, and an ultrasound cart. Other examples include a transducer cable, a transducer cable holder, a docking station for an ultrasound machine, a scanner station configured to hold one or more ultrasound scanners, a needle guide, a battery for a wireless ultrasound scanner, a battery for an ultrasound machine, a registration system, and the like.

The ultrasound systems 1302 and 1304 can be in communication via the network 1306 as part of the environment 1300. The network 1306 can include any suitable network, such as a local area network, a wide area network, a near field communication network, the Internet, an intranet, an extranet, a system bus that couples devices or device components (e.g., in an ASIC, FPGA, or SOC), and combinations thereof. Accordingly, in embodiments, information can be communicated to the ultrasound systems 1302 and 1304 through the network 1306. For instance, the database 1308 can store instructions executable by a processor system of the ultrasound systems 1302 and 1304 and communicate the instructions via the network 1306. The database 1308 can store ultrasound examination data as part of a medical archiver, e.g., a VNA and share the data with the ultrasound systems 1302 and 1304.

The environment 1300 also includes a server system 1310 that can implement any of the functions described herein. The server system 1310 can be a separate device from the ultrasound systems 1302 and 1304. Alternatively, the server system 1310 can be included in at least one of the ultrasound systems 1302 and 1304. In one example, the server system 1310 and the database 1308 are included in at least one of the ultrasound systems 1302 and 1304. In an example, the server system 1310 is implemented as a remote server system that is remote from (e.g., not collocated with) the ultrasound systems 1302 and 1304.

Example Needles

In some embodiments, an ultrasound system in accordance with some embodiments uses an echogenic needle, e.g., a needle with one or more markings that can be detected via ultrasound. For example, FIG. 14 illustrates example needles 1400 for ultrasonic needle localization in accordance with some embodiments. Referring to FIG. 14, the example needles 1400 include needle 1402 that includes dips (e.g., cut outs) on the needle shaft. The lengths of the cut outs are greater than the than the ultrasound spatial resolution, so that the cut-outs can be resolved (e.g., imaged) by the ultrasound system. The example needles 1400 also include needle 1404 that includes bumps (or high spots) on the needle shaft. The lengths of the high spots are greater than the than the ultrasound spatial resolution, so that the cut-outs can be resolved (e.g., imaged) by the ultrasound system.

The example needles 1400 also include needle 1406 that includes a mixture of cut outs and high spots with different sizes/distances. The sizes of the cut outs and high spots can be arranged in a pattern that is known to the ultrasound system and that can be decoded by the ultrasound system. For instance, the pattern can be data bearing, and indicate any suitable information. In an example, the information of the pattern includes an indicator of whether or not the needle 1406 includes the one or more ultrasound transducers 308, e.g., at the tip of the needle. If the decoded information indicates that the needle 1406 includes an ultrasound transducer 308, the system can then instruct the ultrasound transducer 308 (e.g., via the controller 316), to begin to transmit the ultrasound 310 that can be detected by the ultrasound array 302 (see FIG. 3). Hence, the decoding of the information in the sequence embedded on the needle 1406 acts as a trigger signal for the system to initiate ultrasonic needle localization. In some embodiments, if the decoded information indicates that the needle 1406 includes an ultrasound transducer 308, the system can then instruct the ultrasound transducer 308 (e.g., via the controller 316), to receive the ultrasound 310 that can be transmitted by the ultrasound array 302.

The example needles 1400 also include needle 1408 that includes varying diameters on its shaft. The diameters can indicate to the system to trigger the needle 1408 to transmit ultrasound 310 that can be detected by the ultrasound array 302. The example needles 1400 also include needle 1410 that includes hash marks and text, e.g., numbers and/or letters. The text and/or hash marks can indicate to the system to trigger the needle 1410 to transmit ultrasound 310 that can be detected by the ultrasound array 302. Further, the text and/or hash marks can be imaged by the ultrasound system and act as a ruler to determine a location of the needle tip.

The example needles 1400 also include needles 1412 that include needles with spiral curves on their surface. The spiral curves 1412-1-1412-5 can have different shapes, winding rates, etc. to assist in ultrasonic needle localization.

Example Procedures

Figure 15:
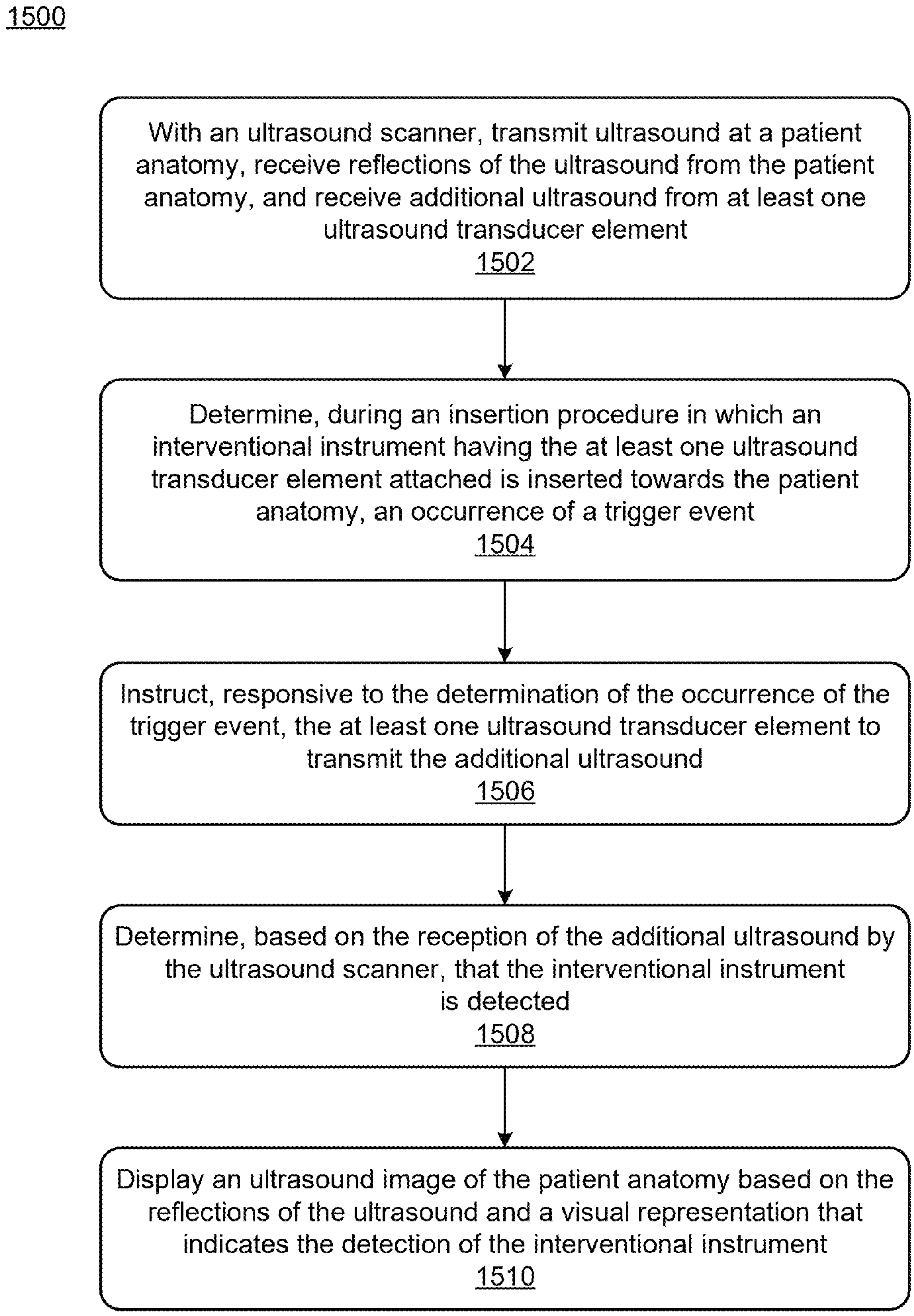
FIG. 15 illustrates an example method for ultrasonic needle localization in accordance with some embodiments.

FIG. 15 illustrates an example method 1500 that can be implemented by an ultrasound system in accordance with some embodiments for ultrasonic needle localization. The ultrasound system can include an ultrasound scanner (e.g., transducer or probe), an ultrasound machine, a processor system, a needle, and a display device. In some embodiments, the ultrasound system includes a computing device having processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem. In some embodiments, the computing device is represented by a computing device as shown in FIG. 12.

Referring to FIG. 15, with an ultrasound scanner, ultrasound is transmitted at a patient anatomy, reflections of the ultrasound from the patient anatomy are received, and additional ultrasound from at least one ultrasound transducer element is received (block 1502). During an insertion procedure in which an interventional instrument having the at least one ultrasound transducer element attached is inserted towards the patient anatomy, an occurrence of a trigger event is determined (block 1504). Responsive to the determination of the occurrence of the trigger event, the at least one ultrasound transducer element is instructed to transmit the additional ultrasound (block 1506). Based on the reception of the additional ultrasound by the ultrasound scanner, it is determined that the interventional instrument is detected (block 1508). An ultrasound image of the patient anatomy based on the reflections of the ultrasound and a visual representation that indicates the detection of the interventional instrument are displayed (1510).

In some embodiments, the interventional instrument includes one or more markings. For instance, the interventional instrument can include one of the example needles 1400 described with respect to FIG. 14 that includes the one or more markings, such as cut-outs, high spots, text, numbers, variable thicknesses or diameters, variable shapes, etc. The ultrasound scanner can image the one or more markings via the ultrasound, and the trigger event can include that the processor system has determined a meaning of the one or more markings. In an example, the meaning of the one or more markings includes that the interventional instrument is equipped with the at least one ultrasound transducer element.

In some embodiments, the ultrasound scanner includes one or more pressure sensors, and the trigger event includes that at least one pressure measured by the one or more pressure sensors is above a threshold pressure. The pressure can be measured via a pressure sensor facing the patient, and indicate that the ultrasound scanner is placed against the patient and ready for use for the needle insertion procedure. Additionally or alternatively, the at least one pressure can indicate that a user has gripped the ultrasound scanner in an orientation suitable for use for the needle insertion procedure. Additionally or alternatively, the ultrasound scanner can include an inertial measurement unit implemented to generate positional data for the ultrasound scanner, and the trigger event can be based on the positional data. For instance, the positional data can indicate that the ultrasound scanner is in proximity to the interventional instrument, the patient, or both.

In some embodiments, the ultrasound scanner is implemented to transmit the ultrasound as interleaved variable-width elevational planes. The trigger event can include that the interventional instrument has crossed the ultrasound of at least one of the elevational planes, as previously described with respect to FIG. 9.

In some embodiments, the ultrasound scanner includes a wearable ultrasound array having at least one hole through which the interventional instrument can be inserted. For example, the ultrasound scanner can include a wearable patch 104-4 as previously described. The at least one hole can include multiple holes, and the processor system can determine, based on the ultrasound image, an insertion hole from among the multiple holes. For instance, the processor system can implement a machine-learned model, such as a neural network, that processes the ultrasound image and generates an inference to select the insertion hole as a recommendation for the insertion of the interventional instrument. The display device can display an indication of the insertion hole as a recommendation for the insertion of the interventional instrument. For example, the display device can display a pattern of the multiple holes, and highlight (e.g., blink) the recommended insertion hole 1126, as previously described by the blinking light in FIG. 11.

In some embodiments, the ultrasound system includes a power source implemented to provide power to the at least one ultrasound transducer element wirelessly from outside of a patient having the patient anatomy. The power source can inductively couple the power through the patient to the at least one ultrasound transducer element. Additionally or alternatively, the ultrasound transmitted by the ultrasound scanner can be converted to energy to power the at least one ultrasound transducer element, such as via a processor or circuit coupled to the at least one ultrasound transducer element. Additionally or alternatively, the ultrasound system can include a battery implemented to provide power to the at least one ultrasound transducer element, and a power source that is separate from the battery that is implemented to provide power to the ultrasound scanner and the processor system.

In some embodiments, the ultrasound scanner includes a first array implemented to transmit the ultrasound and receive the reflections of the ultrasound, and a second array implemented to receive the additional ultrasound. The first array can be implemented to operate at a first ultrasound frequency and the second array can be implemented to operate at a second ultrasound frequency. The first ultrasound frequency can be higher than the second ultrasound frequency. Alternatively, the first ultrasound frequency can be lower than the second ultrasound frequency. Alternatively, the first ultrasound frequency can be equal to the second ultrasound frequency. In some embodiments, the second array is implemented as a single transducer element.

In an example, the ultrasound scanner includes an end portion that is removably attachable to the ultrasound scanner, such as the end portions 520-1 and 520-2 as previously described with respect to FIG. 5. The end portion can configure the ultrasound scanner for wireless coupling to an ultrasound machine in a first configuration and for wired coupling to the ultrasound machine in a second configuration.

Figure 16:
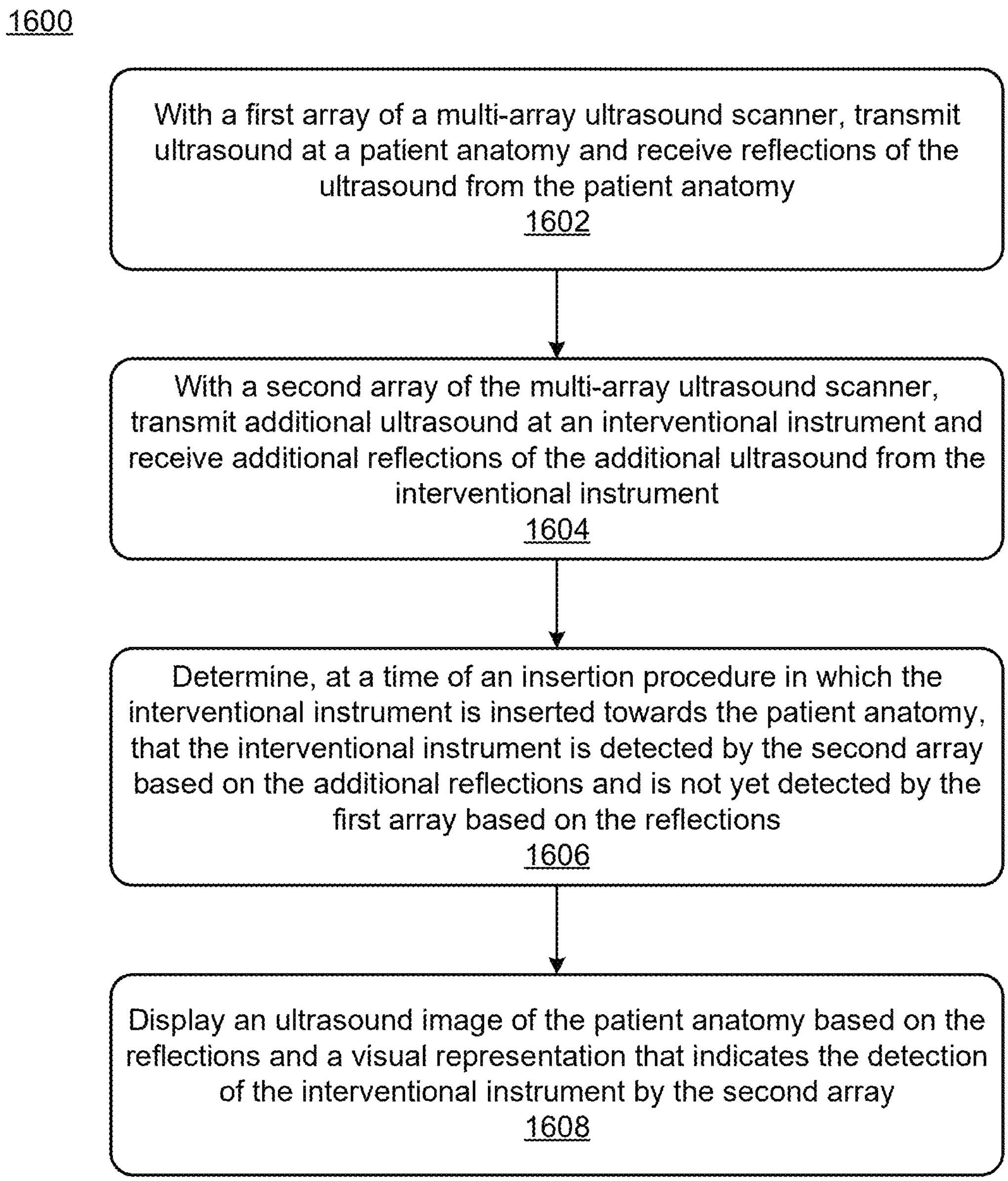
FIG. 16 illustrates an example method for ultrasonic needle localization in accordance with some embodiments.

FIG. 16 illustrates an example method 1600 that can be implemented by an ultrasound system in accordance with some embodiments for ultrasonic needle localization. The ultrasound system can include an ultrasound scanner (e.g., transducer or probe), an ultrasound machine, a processor system, a needle, and a display device. In some embodiments, the ultrasound system includes a computing device having processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem. In some embodiments, the computing device is represented by a computing device as shown in FIG. 12.

Referring to FIG. 16, with a first array of a multi-array ultrasound scanner, ultrasound is transmitted at a patient anatomy and reflections of the ultrasound from the patient anatomy are received (block 1602). With a second array of the multi-array ultrasound scanner, additional ultrasound is transmitted at an interventional instrument and additional reflections of the additional ultrasound from the interventional instrument are received (block 1604). At a time of an insertion procedure in which the interventional instrument is inserted towards the patient anatomy, it is determined that the interventional instrument is detected by the second array based on the additional reflections and is not yet detected by the first array based on the reflections (block 1606). An ultrasound image of the patient anatomy based on the reflections and a visual representation that indicates the detection of the interventional instrument by the second array are displayed (block 1608).

In some embodiments, the processor system is implemented to determine at an additional time of the insertion procedure that the interventional instrument is detected by the first array based on the reflections. The display device can change a display parameter of the visual representation to indicate the interventional instrument is detected by the first array. For example, the change in the display parameter can include to change a color, cause an additional light to be lit, cause an additional button to be highlighted, add text, etc.

In an example, the first array is implemented to transmit the ultrasound at a higher frequency and narrower beam width than the second array is implemented to transmit the additional ultrasound. The second array can be implemented to transmit the additional ultrasound with variable-width elevational planes. The processor system can be implemented to generate a trajectory of a tip of the interventional instrument as it crosses the ultrasound of the variable-width elevational planes during the insertion procedure. The display device can display the trajectory, including to overlay a projection of the trajectory onto the ultrasound image. In one example, the trajectory indicates a current position of the tip of the interventional instrument, such as with a bubble or mark on the trajectory.

In some embodiments, the processor system performs a calibration routine that determines a baseline radio frequency (RF) response from the second array when the interventional instrument is not inserted. The calibration routine can include to subtract the baseline RF response from an RF response generated by the second array during the insertion procedure to determine the detection of the interventional instrument by the second array.

In some embodiments, the first array is implemented to transmit the ultrasound at a first frequency and the second array is implemented to transmit the ultrasound at a second frequency. A ratio of the first frequency and the second frequency can be an irrational number. This frequency allocation can reduce cross coupling, inter-harmonics, spurs, and the like compared to frequency allocations in which the ratio is a rational number. Alternatively, the ratio of the first frequency and the second frequency can be a rational number. In aspects, the first array is implemented to transmit the ultrasound at a first frequency and the second array is implemented to transmit the ultrasound at a second frequency that is a subharmonic of the first frequency.

In some embodiments, the second array includes a single transducer element without including other transducer elements. In other embodiments, the first array includes one or more rows of transducer elements and the second array includes at least one row of additional transducer elements adjacent to the one or more rows of transducer elements.

In some embodiments, the multi-array ultrasound scanner includes a lens configured to be placed over the second array to steer the additional ultrasound. The lens can be removably attached to the multi-array ultrasound scanner. In an example, the lens covers both the first array and the second array. Additionally or alternatively, the multi-array ultrasound scanner can include a substrate onto which the first array and the second array are placed. The substrate can be deformable in shape to steer at least one of the ultrasound and the additional ultrasound. For example, the multi-array ultrasound scanner can comprise a wearable ultrasound patch, such as the patch 104-4 previously described.

Figure 17:
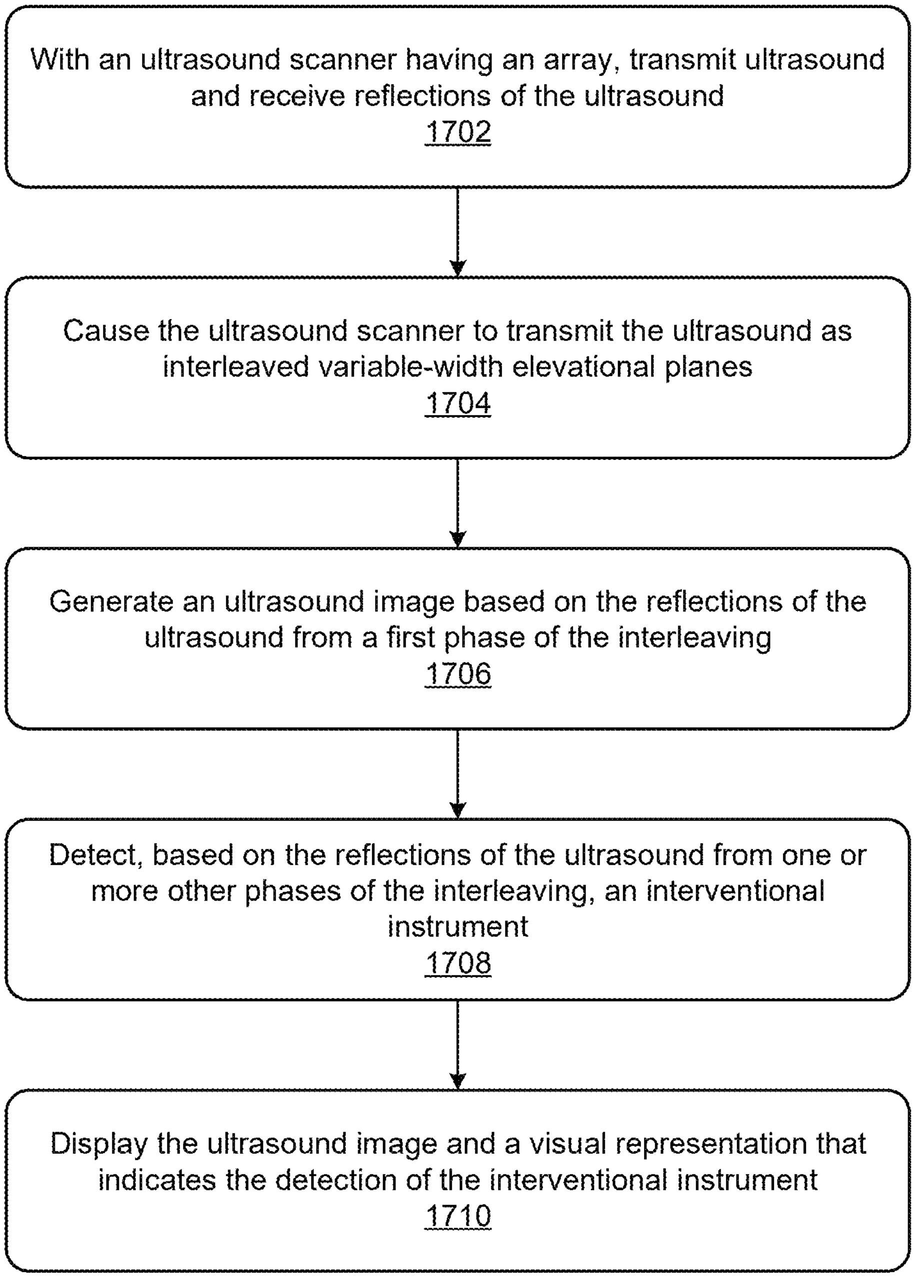
FIG. 17 illustrates an example method for ultrasonic needle localization in accordance with some embodiments.

FIG. 17 illustrates an example method 1700 that can be implemented by an ultrasound system in accordance with some embodiments for ultrasonic needle localization. The ultrasound system can include an ultrasound scanner (e.g., transducer or probe), an ultrasound machine, a processor system, a needle, and a display device. In some embodiments, the ultrasound system includes a computing device having processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem. In some embodiments, the computing device is represented by a computing device as shown in FIG. 12.

Referring to FIG. 17, with an ultrasound scanner having an array, ultrasound is transmitted and reflections of the ultrasound are received (block 1702). The ultrasound scanner is caused to transmit the ultrasound as interleaved variable-width elevational planes (block 1704). An ultrasound image is generated based on the reflections of the ultrasound from a first phase of the interleaving (block 1706). Based on the reflections of the ultrasound from one or more other phases of the interleaving, an interventional instrument is detected (block 1708). The ultrasound image and a visual representation that indicates the detection of the interventional instrument are displayed (block 1710).

In some embodiments, the ultrasound from the first phase of the interleaving has a first beam width in the elevational planes and the ultrasound from the one or more other phases of the interleaving has at least two beam widths that are different from the first beam width in the elevational planes, such as previously described with respect to FIG. 9. The processor system can generate a trajectory of a tip of the interventional instrument as it crosses the variable-width elevational planes of the one or more other phases of the interleaving during the insertion procedure. The display device can display the trajectory or a projection of the trajectory onto an imaging plane of the ultrasound image, such as is illustrated by the trajectory 1130 in FIG. 11.

There are a number of example embodiments described herein.

Example 1 is an ultrasound system having an ultrasound scanner configured to transmit ultrasound at a patient anatomy, receive reflections of the ultrasound from the patient anatomy, and receive additional ultrasound from at least one ultrasound transducer element and an interventional instrument having the at least one ultrasound transducer element attached to the interventional instrument and configured for insertion towards the patient anatomy as part of an insertion procedure. The ultrasound system also has a processor system configured to: determine, during the insertion procedure, an occurrence of a trigger event; instruct, responsive to the determination of the occurrence of the trigger event, the at least one ultrasound transducer element to transmit the additional ultrasound; and determine, based on the reception of the additional ultrasound by the ultrasound scanner, that the interventional instrument is detected. The ultrasound system further includes a display device configured to display an ultrasound image of the patient anatomy based on the reflections of the ultrasound and a visual representation that indicates the detection of the interventional instrument.

Example 2 is the ultrasound system of example 1 that may optionally include that the interventional instrument includes one or more markings, the ultrasound scanner is implemented to image the one or more markings via the ultrasound, and the trigger event includes that the processor system has determined a meaning of the one or more markings.

Example 3 is the ultrasound system of example 2 that may optionally include that the meaning of the one or more markings includes that the interventional instrument is equipped with the at least one ultrasound transducer element.

Example 4 is the ultrasound system of example 1 that may optionally include that the ultrasound scanner includes one or more pressure sensors, and the trigger event includes that at least one pressure measured by the one or more pressure sensors is above a threshold pressure.

Example 5 is the ultrasound system of example 1 that may optionally include that the ultrasound scanner is implemented to transmit the ultrasound as interleaved variable-width elevational planes, and the trigger event includes that the interventional instrument has crossed the ultrasound of at least one of the elevational planes.

Example 6 is the ultrasound system of example 1 that may optionally include that the ultrasound scanner includes an inertial measurement unit implemented to generate positional data for the ultrasound scanner, and the trigger event is based on the positional data.

Example 7 is the ultrasound system of example 1 that may optionally include that the ultrasound scanner includes a wearable ultrasound array having at least one hole through which the interventional instrument can be inserted.

Example 8 is the ultrasound system of example 7 that may optionally include that the at least one hole includes multiple holes, the processor system is implemented to determine, based on the ultrasound image, an insertion hole from among the multiple holes, and the display device is implemented to display an indication of the insertion hole as a recommendation for the insertion of the interventional instrument.

Example 9 is the ultrasound system of example 1 that may optionally include a power source implemented to provide power to the at least one ultrasound transducer element wirelessly from outside of a patient having the patient anatomy.

Example 10 is the ultrasound system of example 1 that may optionally include a battery implemented to provide power to the at least one ultrasound transducer element, and a power source that is separate from the battery that is implemented to provide power to the ultrasound scanner and the processor system.

Example 11 is the ultrasound system of example 1 that may optionally include that the ultrasound scanner includes a first array implemented to transmit the ultrasound and receive the reflections of the ultrasound, and a second array implemented to receive the additional ultrasound.

Example 12 is the ultrasound system of example 11 that may optionally include that the first array is implemented to operate at a first ultrasound frequency and the second array is implemented to operate at a second ultrasound frequency, the first ultrasound frequency being higher than the second ultrasound frequency.

Example 13 is the ultrasound system of example 11 that may optionally include that the second array is implemented as a single transducer element.

Example 14 is the ultrasound system of example 1 that may optionally include that the ultrasound scanner includes an end portion that is removably attachable to the ultrasound scanner, the end portion configuring the ultrasound scanner for wireless coupling to an ultrasound machine in a first configuration and for wired coupling to the ultrasound machine in a second configuration.

Example 15 is an ultrasound system having: a multi-array ultrasound scanner having a first array configured to transmit ultrasound at a patient anatomy and receive reflections of the ultrasound from the patient anatomy, and a second array configured to transmit additional ultrasound at an interventional instrument and receive additional reflections of the additional ultrasound from the interventional instrument, where the interventional instrument configured for insertion towards the patient anatomy as part of an insertion procedure; a processor system and a display device. The processor system is configured to determine at a time of the insertion procedure that the interventional instrument is detected by the second array based on the additional reflections and is not yet detected by the first array based on the reflections. The display device is configured to display an ultrasound image of the patient anatomy based on the reflections and a visual representation that indicates the detection of the interventional instrument by the second array.

Example 16 is the ultrasound system of example 15 that may optionally include that the processor system is implemented to determine at an additional time of the insertion procedure that the interventional instrument is detected by the first array based on the reflections, wherein the display device is implemented to change a display parameter of the visual representation to indicate the interventional instrument is detected by the first array.

Example 17 is the ultrasound system of example 15 that may optionally include that the first array is implemented to transmit the ultrasound at a higher frequency and narrower beam width than the second array is implemented to transmit the additional ultrasound.

Example 18 is the ultrasound system of example 17 that may optionally include that the second array is implemented to transmit the additional ultrasound with variable-width elevational planes, and the processor system is implemented to generate a trajectory of a tip of the interventional instrument as it crosses the ultrasound of the variable-width elevational planes during the insertion procedure.

Example 19 is the ultrasound system of example 18 that may optionally include that the display device is implemented to overlay a projection of the trajectory onto the ultrasound image.

Example 20 is the ultrasound system of example 19 that may optionally include that the trajectory indicates a current position of the tip of the interventional instrument.

Example 21 is the ultrasound system of example 15 that may optionally include that the processor system is implemented to perform a calibration routine that determines a baseline radio frequency (RF) response from the second array when the interventional instrument is not inserted, and subtracts the baseline RF response from an RF response generated by the second array during the insertion procedure to determine the detection of the interventional instrument by the second array.

Example 22 is the ultrasound system of example 15 that may optionally include that the first array is implemented to transmit the ultrasound at a first frequency and the second array is implemented to transmit the ultrasound at a second frequency, a ratio of the first frequency and the second frequency being an irrational number.

Example 23 is the ultrasound system of example 15 that may optionally include that the first array is implemented to transmit the ultrasound at a first frequency and the second array is implemented to transmit the ultrasound at a second frequency that is a subharmonic of the first frequency.

Example 24 is the ultrasound system of example 15 that may optionally include that the second array includes a single transducer element without including other transducer elements.

Example 25 is the ultrasound system of example 15 that may optionally include that the first array includes one or more rows of transducer elements and the second array includes at least one row of additional transducer elements adjacent to the one or more rows of transducer elements.

Example 26 is the ultrasound system of example 15 that may optionally include that the multi-array ultrasound scanner includes a lens configured to be placed over the second array to steer the additional ultrasound.

Example 27 is the ultrasound system of example 15 that may optionally include that the multi-array ultrasound scanner includes a substrate onto which the first array and the second array are placed, the substrate being deformable in shape to steer at least one of the ultrasound and the additional ultrasound.

Example 28 is an ultrasound system having: an ultrasound scanner having an array configured to transmit ultrasound and receive reflections of the ultrasound; an interventional instrument configured for patient insertion as part of an insertion procedure; a processor system and a display device. The processor system is configured to: cause the ultrasound scanner to transmit the ultrasound as interleaved variable-width elevational planes; generate an ultrasound image based on the reflections of the ultrasound from a first phase of the interleaving; and detect the interventional instrument based on the reflections of the ultrasound from one or more other phases of the interleaving. The display device is configured to display the ultrasound image and a visual representation that indicates the detection of the interventional instrument.

Example 29 is the ultrasound system of example 28 that may optionally include that the ultrasound from the first phase of the interleaving has a first beam width in the elevational planes and the ultrasound from the one or more other phases of the interleaving has at least two beam widths that are different from the first beam width in the elevational planes.

Example 30 is the ultrasound system of example 29 that may optionally include that the processor system is implemented to generate a trajectory of a tip of the interventional instrument as it crosses the variable-width elevational planes of the one or more other phases of the interleaving during the insertion procedure.

Example 31 is the ultrasound system of example 30 that may optionally include that the display device is implemented to display the trajectory or a projection of the trajectory onto an imaging plane of the ultrasound image.

Example 32 is a method including the operations performed by the ultrasound system of one or more of examples 1-31.

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in some embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

We claim:

1. An ultrasound system comprising:

an ultrasound scanner configured to transmit first ultrasound at a patient anatomy, receive reflections of the first ultrasound from the patient anatomy, and receive additional ultrasound from at least one ultrasound transducer element, wherein the ultrasound scanner is implemented to transmit the first ultrasound as interleaved variable-width elevational planes;

an interventional instrument having the at least one ultrasound transducer element attached to the interventional instrument and configured for insertion towards the patient anatomy as part of an insertion procedure;

a processor system configured to:

determine, during the insertion procedure, an occurrence of a trigger event, wherein the trigger event includes that the interventional instrument has crossed the first ultrasound of at least one of the elevational planes;

instruct, responsive to the determination of the occurrence of the trigger event, the at least one ultrasound transducer element to transmit the additional ultrasound; and determine, based on the reception of the additional ultrasound by the ultrasound scanner, that the interventional instrument is detected; and a display device configured to display an ultrasound image of the patient anatomy based on the reflections of the first ultrasound and a visual representation that indicates the detection of the interventional instrument.

2. The ultrasound system as described in claim 1, wherein the interleaved variable-width elevational planes include a plurality of interleaved elevational beams at different frequencies and with differences in thickness.

3. The ultrasound system as described in claim 2 wherein the interleaved variable-width elevational planes include first and second elevational beams with the first elevational beam being generated by higher frequency ultrasound than the second elevational beam and being narrower than the second elevational beam.

4. The ultrasound system as described in claim 2 further comprising an interleaver to interleave the interleaved variable-width elevational planes.

5. The ultrasound system as described in claim 2 wherein the ultrasound scanner comprises a multi-array ultrasound scanner operable to generate interleaved variable-width elevational planes simultaneously using a different array to transmit a different one of the interleaved variable-width elevational planes.

6. The ultrasound system as described in claim 5 wherein the multi-array ultrasound scanner has a center array that operates at a first frequency and at least one array on each side the center array that operate at frequencies that are less than the first frequency.

7. The ultrasound system as described in claim 6 wherein the center array is for patient and in-plane interventional instrument visualization and the at least one array on each side of the center array being for interventional instrument localization based on frequencies.

8. The ultrasound system as described in claim 1, wherein the ultrasound scanner includes a wearable ultrasound array having at least one hole through which the interventional instrument can be inserted.

9. The ultrasound system as described in claim 8, wherein the at least one hole includes multiple holes, the processor system is implemented to determine, based on the ultrasound image and prior to insertion of the interventional instrument, an insertion hole from among the multiple holes, and the display device is implemented to display an indication of the insertion hole as a recommendation for the insertion of the interventional instrument.

10. The ultrasound system as described in claim 1, further comprising a battery implemented to provide power to the at least one ultrasound transducer element, and a power source that is separate from the battery that is implemented to provide power to the ultrasound scanner and the processor system.

11. The ultrasound system as described in claim 1, wherein the ultrasound scanner includes a first array implemented to transmit the first ultrasound and receive the reflections of the first ultrasound, and a second array implemented to receive the additional ultrasound, and further wherein the first array is implemented to operate at a first ultrasound frequency and the second array is implemented to operate at a second ultrasound frequency, the first ultrasound frequency being higher than the second ultrasound frequency.

12. The ultrasound system as described in claim 1, wherein the ultrasound scanner includes a first array implemented to transmit the first ultrasound and receive the reflections of the first ultrasound, and a single transducer element implemented to receive the additional ultrasound.

13. The ultrasound system as described in claim 1, wherein the ultrasound scanner includes an end portion that is removably attachable to the ultrasound scanner, the end portion configuring the ultrasound scanner for wireless coupling to an ultrasound machine in a first configuration and for wired coupling to the ultrasound machine in a second configuration.

14. The ultrasound system as described in claim 1 wherein the processor system is configured to determine a trajectory of interventional instrument based on detection of the interventional instrument intersecting multiple elevation planes of the interleaved variable-width elevational planes over time.

15. The ultrasound system as described in claim 14 wherein the processor system is configured to project the trajectory onto an imaging plane to the trajectory via a user interface on the display device.

16. The ultrasound system as described in claim 14 wherein the ultrasound scanner includes a first array implemented to transmit the interleaved variable-width elevational planes.

17. The ultrasound system as described in claim 14 wherein the interleaver is operable to interleave beams for imaging with beams for the interleaved variable-width elevational planes.

18. An ultrasound system comprising:

an ultrasound scanner having a multi-array transducer configured to transmit first ultrasound at a patient anatomy, receive reflections of the first ultrasound from the patient anatomy, and receive additional ultrasound from at least one ultrasound transducer element, wherein the multi-array transducer is configured to generate interleaved variable-width elevational planes simultaneously using a different array to transmit a different one of the interleaved variable-width elevational planes;

an interventional instrument having the at least one ultrasound transducer element attached to the interventional instrument and configured for insertion towards the patient anatomy as part of an insertion procedure;

a processor system configured to:

determine, during the insertion procedure, an occurrence of a trigger event, wherein the interventional instrument has crossing the first ultrasound of at least one of the elevational planes of one or more outer arrays of the multi-array transducer;

instruct, responsive to the determination of the occurrence of the trigger event, the at least one ultrasound transducer element to transmit the additional ultrasound; and determine, based on the reception of the additional ultrasound by the ultrasound scanner, that the interventional instrument is detected; and a display device configured to display an ultrasound image of the patient anatomy based on the reflections of the first ultrasound and a visual representation that indicates the detection of the interventional instrument.

19. The ultrasound system as described in claim 18 wherein the ultrasound scanner comprises a multi-array ultrasound scanner operable to generate interleaved variable-width elevational planes simultaneously using a different array to transmit a different one of the interleaved variable-width elevational planes.

20. The ultrasound system as described in claim 19 wherein the multi-array ultrasound scanner has a center array that operates at a first frequency and at least one array on each side the center array that operate at frequencies that are less than the first frequency.

21. The ultrasound system as described in claim 18 wherein the processor system is configured to determine a trajectory of interventional instrument based on detection of the interventional instrument intersecting multiple elevation planes of the interleaved variable-width elevational planes over time.

* * * * *